US008435791B2

(12) United States Patent
Galun et al.

(10) Patent No.: US 8,435,791 B2
(45) Date of Patent: May 7, 2013

(54) CONTROLLED LASER TREATMENT FOR NON-INVASIVE TISSUE ALTERATION, TREATMENT AND DIAGNOSTICS WITH MINIMAL COLLATERAL DAMAGE

(75) Inventors: Eithan Galun, Har Adar (IL); Aaron Lewis, Jerusalem (IL); Evelyne Zeira, Bet-Shemesh (IL); Alexandra Manevitch, Jerusalem (IL); Artium Khatchatouriants, Jerusalem (IL); Yitzchak Hemo, Jerusalem (IL)

(73) Assignees: Hadasit Medical Research Services and Development Ltd., Jerusalem (IL); Yissum Research Development Company of the Hebrew University of Jerusalem, Jerusalem (IL)

(*) Notice: Subject to any disclaimer, the term of this patent is extended or adjusted under 35 U.S.C. 154(b) by 607 days.

(21) Appl. No.: 10/508,531

(22) PCT Filed: Mar. 27, 2003

(86) PCT No.: PCT/IL03/00260
§ 371 (c)(1),
(2), (4) Date: Dec. 8, 2005

(87) PCT Pub. No.: WO03/099883
PCT Pub. Date: Oct. 2, 2003

(65) Prior Publication Data
US 2006/0100611 A1 May 11, 2006

Related U.S. Application Data

(60) Provisional application No. 60/367,509, filed on Mar. 27, 2002.

(51) Int. Cl.
*C12N 15/87* (2006.01)
(52) U.S. Cl.
USPC ............ 435/460; 435/455; 435/456; 435/459
(58) Field of Classification Search ........................ None
See application file for complete search history.

(56) References Cited

U.S. PATENT DOCUMENTS

| 4,775,361 | A | | 10/1988 | Jacques et al. |
| 5,272,072 | A | | 12/1993 | Kaneko et al. |
| 5,330,467 | A | | 7/1994 | Abela |
| 5,586,982 | A | | 12/1996 | Abela |
| 5,658,565 | A | | 8/1997 | Billiar et al. |
| 5,702,384 | A | * | 12/1997 | Umeyama et al. ......... 604/892.1 |
| 5,713,845 | A | | 2/1998 | Tankovich |
| 6,071,276 | A | | 6/2000 | Abela |
| 6,190,380 | B1 | | 2/2001 | Abela |
| 6,251,099 | B1 | | 6/2001 | Kollias et al. |
| 6,337,462 | B1 | * | 1/2002 | Smart ...................... 219/121.68 |
| 2002/0016533 | A1 | * | 2/2002 | Marchitto et al. ............ 600/310 |

FOREIGN PATENT DOCUMENTS

| WO | WO 98/33444 | 8/1998 |
| WO | WO 03/079883 | 10/2003 |

OTHER PUBLICATIONS

Nussbaum et al., A review of laser technology and light-tissue interactions as background to therapeutic applications of low intensity lasers and other sources, Physical Therapy Reviews 8: 31-44, 2003.*
Pouton and Seymour, Key issues in non-viral gene delivery, Adv Drug Deliv Rev. 46(1-3): 187-203, 2001.*
Read et al., Barriers to gene delivery using synthetic vectors, Adv Genet. 53: 19-46, 2005.*
Dobson, Gene therapy progress and prospects: magnetic nanoparticle-based gene delivery. Gene Ther. 13(4): 283-7, 2006.*
Shoji et al., Current status of delivery systems to improve target efficacy of oligonucleotides. Current Pharmaceutical Design 10(7): 785-96, 2004.*
Tirlapur et al. Femtosecond near-infrared laser pulse induced strand breaks in mammalian cells. Cell Mol Biol (Noisy-le-grand). 47 Online Pub: OL131-134, 2001 (one page abstract provided).*
Campagnola et al. High-resolution nonlinear optical imaging of live cells by second harmonic generation. Biophys J. 77(6):3341-9, 1999.*
Loesel et al., Non-thermal ablation of neural tissue with femtosecond laser pulses, Appl. Phys. B 66, 121-128, 1998.*
Koga et al., Selective transvascular delivery of oligodeoxynucleotides to experimental brain tumors, J Neurooncol. 43(2):143-51, 1999.*
Wilson et al. "Sensitisation of *Candida albicans* to Killing by Low-Power Laser Light", Journal of Oral Pathology Medicine, 22: 354-357, 1993. Esp. p. 335, 356.
Messner et al. "Generation of Tunable, Ultrashort THz Radiation Up to 5.3 THz", SPIE., 3265: 136-147, 1998. Esp. p. 140-142.
Haglund et al. "Surface Modification and Ablation of Insulators Using A Tunable, Picosecond Mid-Infrared Laser", Materials Research Society Symposium Proceedings, 526: 3-14, 1998. Esp. p. 10-13.
Ciulla et al. "Changing Therapeutic Paradigms for Exudative Age-Related Macular Degeneration: Antiangiogenic Agents and Photodynamic Therapy", Experimental Opinion Investigative Drugs, 8(12): 2173-2182, 1999. Esp. p. 2177, 2178.
Parish et al. "Isolation and One-Step Preparation of A2E and Iso-A2E, Fluorophores From Human Retinal Pigment Epithelium", Proc. Natl. Acad. Sci. USA, 95: 14609-14613, 1998.
Aiuti et al. "Correction of ADA-SCID by Stem Cell Gene Therapy Combined With Nonmyeloablative Conditioning", Science, 296: 2410-2413, 2002.
Babiuk et al. "Electroporation Improves the Efficacy of DNA Vaccines in Large Animals", Vaccine, 20: 3399-3408, 2002.
Bartlett et al. "In Vivo Targeted Repair of A Point Mutation in the Canine Dystrophin Gene by A Chimeric RNA/DNA Oligonucleotide", Nature Biotechnology, 18: 615-622, 2000.
Bettan et al. "High-Level Protein Secretion Into Blood Circulation After Electric Pulse-Mediated Gene Transfer Into Skeletal Muscle", Molecular Therapy, 2(3): 204-210, 2000.
Blair-Parks et al. "High-Level Gene Transfer to the Cornea Using Electroporation", The Journal of Gene Medicine, 4: 92-100, 2002.

(Continued)

Primary Examiner — Deborah Crouch

(57) ABSTRACT

A highly controlled and precise system, device and method for tissue and cellular alteration and treatment below or at surfaces with a laser. The present invention is characterized by ultra low levels of collateral damage as defined by physiologically relevant tests that measure tissue viability. The operation of the present invention is based on spectrally confining the interaction between laser energy and a targeted tissue including an essential element for physiologically relevant tests for monitoring tissue viability.

41 Claims, 22 Drawing Sheets

OTHER PUBLICATIONS

Durieux et al. "High-Efficiency Gene Electrotransfer Into Skeletal Muscle: Description and Physiological Applicability of A New Pulse Generator", Biochemical and Biophysical Research Communications, 296: 443-450, 2002.
Endoh et al. "Fetal Gene Transfer by Intrauterine Injection With Microbubble-Enhanced Ultrasound", Molecular Therapy, 5(5): 501-508, 2002.
Ferber "Gene Therapy: Safer and Virus-Free?", Science, 294: 1638-1642, 2001.
Hacein-Bey-Abina et al. "Sustained Correction of X-Linked Severe Combined Immunodeficiency by Ex Vivo Gene Therapy", The New England Journal of Medicine, 346(16): 1185-1193, 2002.
Honigman et al. "Imaging Transgene Expression in Live Animals", Molecular Therapy, 4(3): 239-249, 2001.
Lefesvre et al. "A Comparison of Efficacy and Toxicity Between Electroporation and Adenoviral Gene Transfer", BMC Molecular Biology, 3: 1-13, 2002.
Lewin et al. "Tat Peptide-Derivatized Magnetic Nanoparticles Allow In Vivo Tracking and Recovery of Progenitor Cells", Nature Biotechnology, 18: 410-414, 2000.
Luo et al. "Synthetic DNA Delivery Systems", Nature Biotechnology, 18: 33-37, 2000.
Mikszta et al. "Improved Genetic Immunization Via Micromechanical Disruption of Skin-Barrier Function and Targeted Epidermal Delivery", Nature Medicine, 8(4): 415-419, 2002.
Pfeifer et al. "Gene Therapy: Promises and Problems", Annual Reviews of Genomic and Human Genetics, 2: 177-211, 2001.
Somia et al. "Gene Therapy: Trials and Tribulations", Nature Reviews/Genetics, 1: 91-99, 2000.
Somiari et al. "Theory and In Vivo Application of Electroporative Gene Delivery", Molecular Therapy, 2(3): 178-187, 2000.
Sullenger et al. "Emerging Clinical Applications of RNA", Nature, 418: 252-258, 2002.
Tirlapur et al. "Targeted Transfection by Femtosecond Laser", Nature, 418: 290, 2002.
Yant et al. "Somatic Integration and Long-Term Transgene Expression in Normal and Haemophilic Mice Using a DNA Transposon System", Nature Genetics, 25: 35-41, 2000.
Zhang et al. "Efficient Expression of Naked DNA Delivered Intraarterially to Limb Muscles of Nonhuman Primates", Human Gene Therapy, 12: 427-438, 2001.
Communication Pursuant to Article 94(3) EPC Dated Jan. 12, 2011 From the European Patent Office Re. Application No. 03710203.5.
Invitation Pursuant to Rule 63(1) EPC Dated Aug. 2, 2010 From the European Patent Office Re. Application No. 03710203.5.
Response Dated Sep. 27, 2010 to Invitation Pursuant to Rule 63(1) EPC of Aug. 2, 2010 From the European Patent Office Re. Application No. 03710203.5.
Supplementary European Search Report Dated Oct. 8, 2010 From the European Patent Office Re. Application No. 03710203.5.
Response Dated Jul. 12, 2011 to Communication Pursuant to Article 94(3) EPC of Jan. 12, 2011 From the European Patent Office Re. Application No. 03710203.5.
Düchler et al. "Somatic Gene Transfer Into the Lactating Ovine Mammary Gland", The Journal of Gene Medicine, 4: 282-291, 2002.
Duguez et al. "Mitochondrial Biogenesis During Skeletal Muscle Regeneration", American Journal of Physiology, Endocrinological Metabolism, 282: E802-E809, 2002.
Ortiz-Urda et al. "Stable Nonviral Genetic Correction of Inherited Human Skin Disease", Nature Medicine, 8(10): 1166-1170, 2002.
Pfeifer et al. "Gene Therapy: Promises and Problems", Annual Reviews of Genomics and Human Genetics, 2: 177-211, 2001.
Rebuffat et al. "Selective Enhancement of Gene Transfer by Steroid-Mediated Gene Delivery", Nature Biotechnology, 19: 1155-1161, 2001.

* cited by examiner

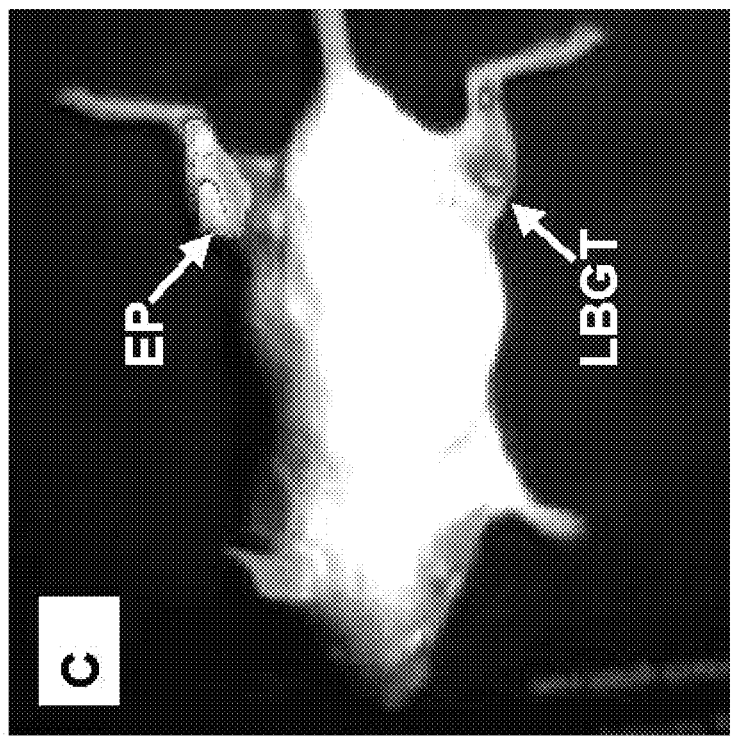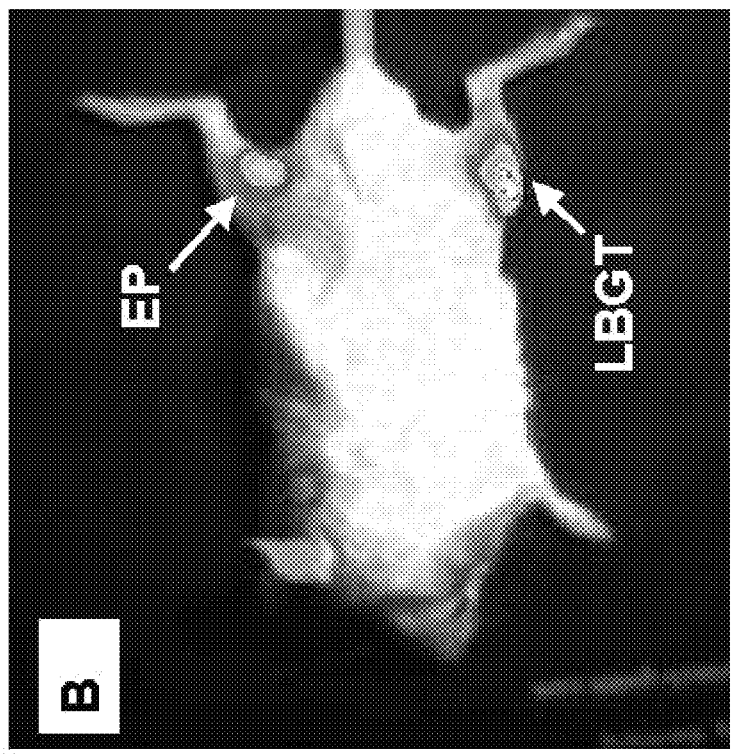

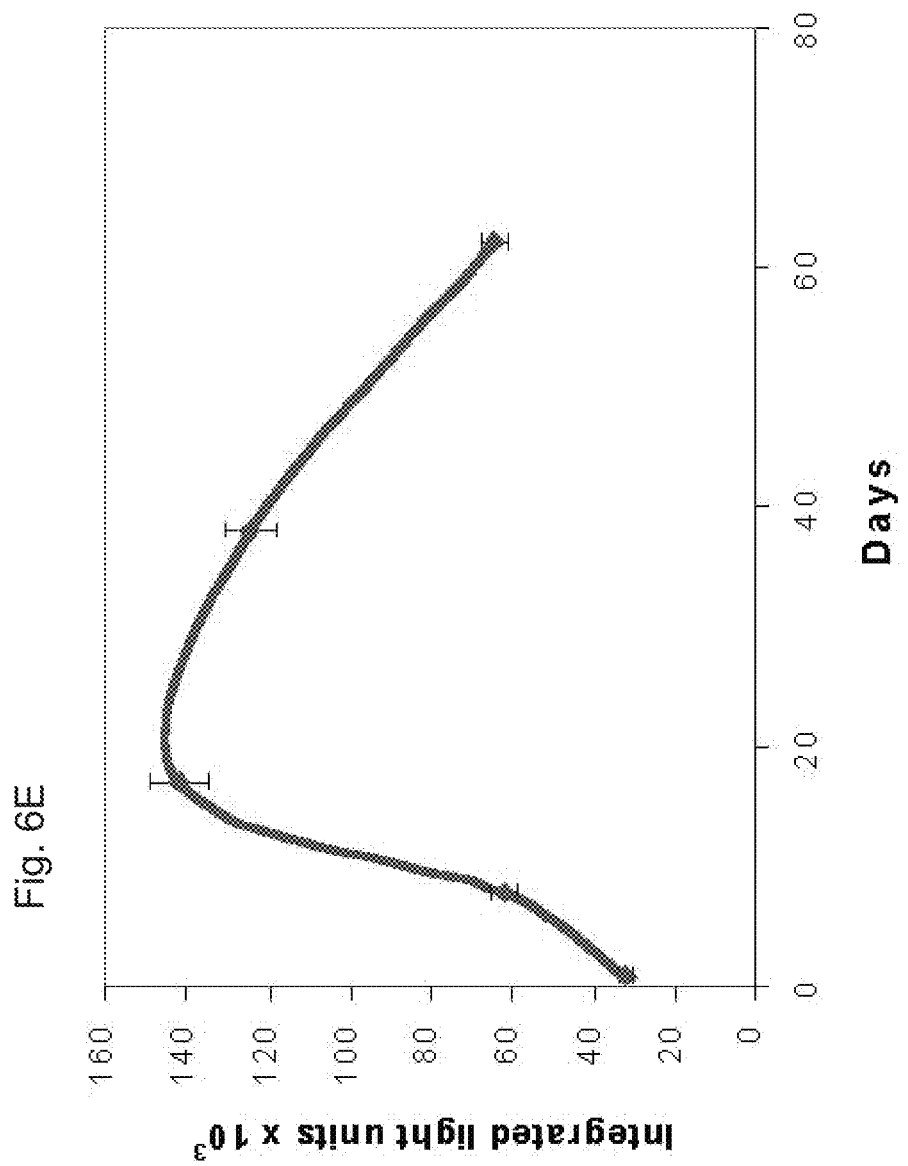

Day 1

Day 48

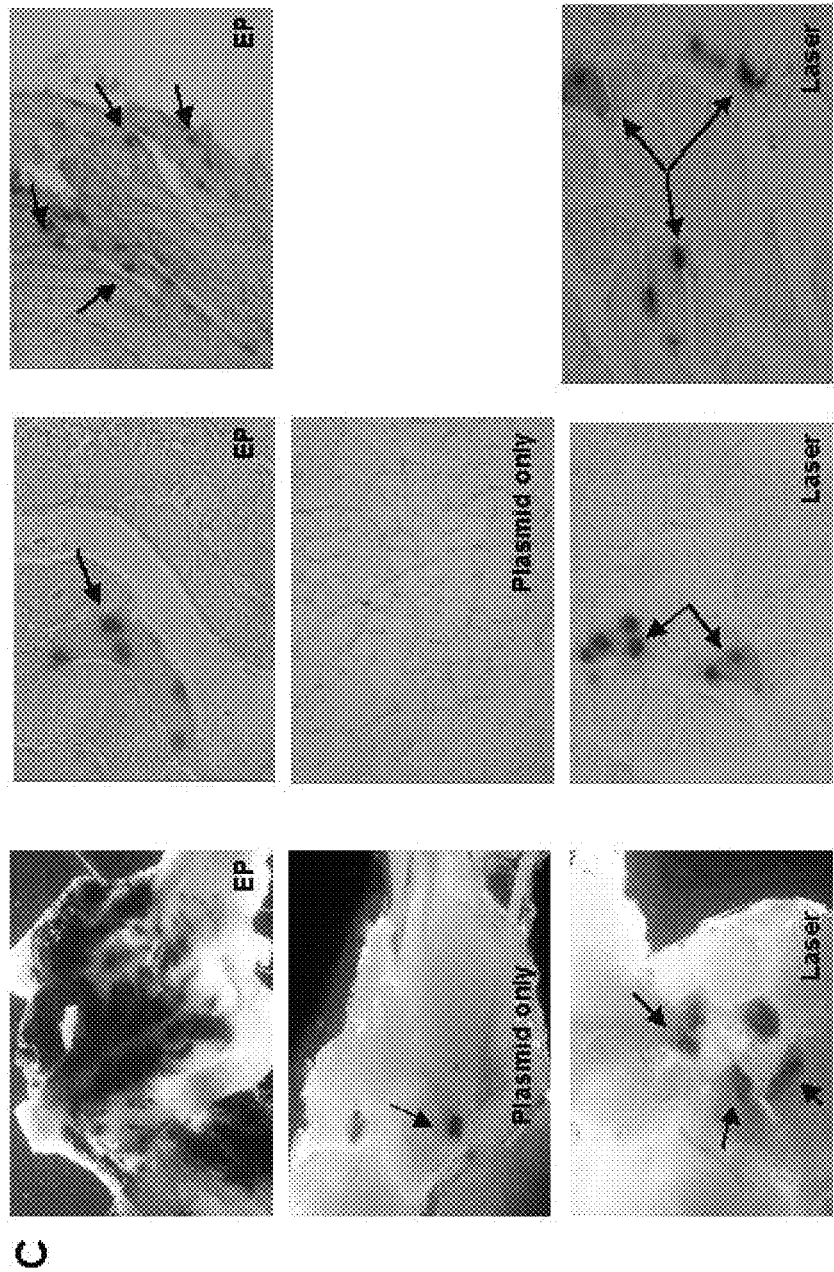

70 Days

48 Hours

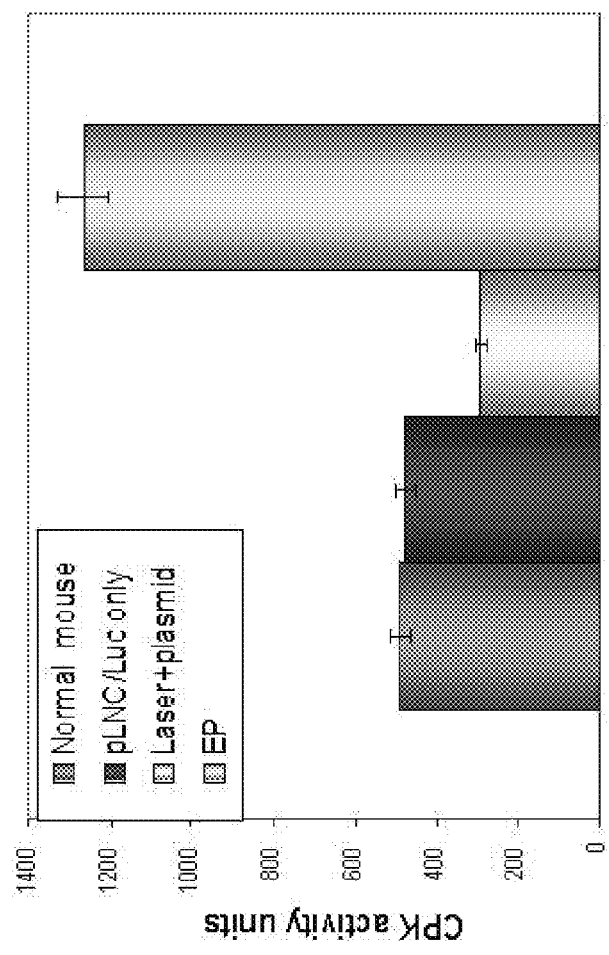

Figure 13
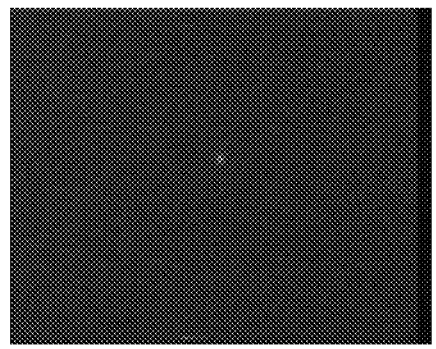
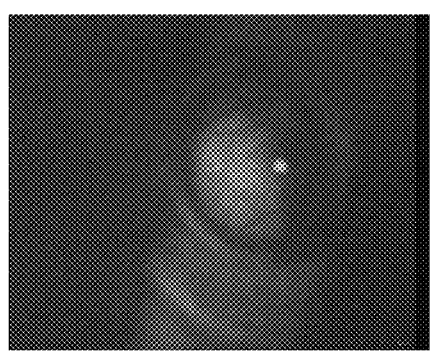
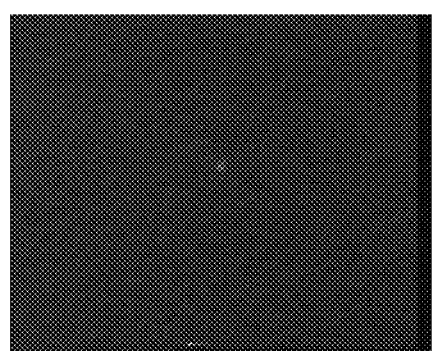
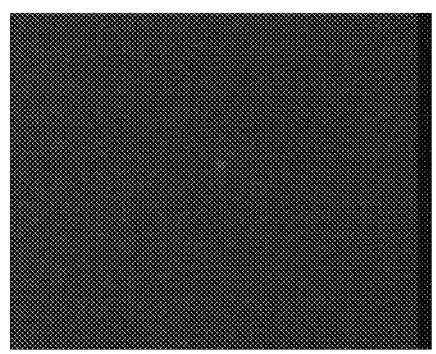
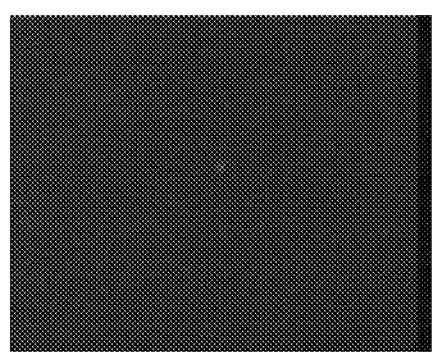

The Rate of Bleaching

CONTROLLED LASER TREATMENT FOR NON-INVASIVE TISSUE ALTERATION, TREATMENT AND DIAGNOSTICS WITH MINIMAL COLLATERAL DAMAGE

RELATED PATENT APPLICATION

This application is a National Phase Application of PCT/IL03/00260 having International Filing Date of 27 Mar. 2003, which claims priority from U.S. Provisional Patent Application No. 60/367,509 filed 27 Mar. 2002.

FIELD OF INVENTION

The present invention is of a system, device and method for tissue and cellular alteration and treatment below or at surfaces with a laser, and in particular, of such a system, device and method which at least reduces collateral damage.

BACKGROUND OF THE INVENTION

All human disease develops as a result from alterations in genetic or environmental factors or the combination of both. Cardiovascular diseases, which are the world's leading cause of death, are the best examples. In this disease genetic and environmental factors "join" to induce the endothelial pathology leading to cardiovascular and heart disease. Systemic and local delivery of genes or gene expression modifying agents could serve as the future arm of therapy. To achieve this, a temporary alteration to a particular layer of tissue below the surface of tissue, which forms pores without perturbing the overlying tissue, is needed for the facilitated entry of genetic material.

Some genetically based diseases result in disease states that can be retarded even without the addition of genetic material. They require alteration and diagnosis of a specific component below the surface of the tissue without perturbing the overlying tissue. The nature of the required alteration can extend from permanent destruction through a bleaching of a certain component of the tissue. An example of such a disease is called age related macular degeneration (AMD) in which a pigment that accumulates behind the retina has to be bleached under conditions that do not touch the overlying retinal tissue.

There are also infections that require a total destruction of tissue without affecting the overlying and underlying tissue. An example is a fungal infection in an underlying tissue layer that must be removed without damaging the overlying tissue. A specific case is fungal infection under cutaneous tissue like the nail of the foot that has to be destroyed without damaging the overlying or underlying tissue.

All of these problems have been incredibly difficult to address with existing technology. For example, successful solutions to these problems require effective calibration with a defined, in vivo, methodology for depth of penetration and the exact parameters required for minimal collateral damage. These parameters have to be checked with a defined diagnostic procedure, other than standard pathological techniques that are filled with artifacts from the fixation procedure. Thus, standard pathology is incapable of defining, with the sensitivity required, the parameters for highly controlled treatment.

Laser methods have been applied in the past to each of the problems previously described, but with limited success. All of these previous applications have used a linear form of laser tissue interaction, which cannot highlight a specific tissue layer selectively without an injection of an external highlighting light absorbing agent, which is the case for palliative laser attempts for AMD progress retardation using photodynamic therapy (see H. Sun and J. Nathans, "The Challenge of Macular Degeneration," Scientific American, October 2001, p 61). Except for such protocols, in which injection of a highlighting absorbing substance is required, all other laser methodologies that have been applied to these problems have an effect of the laser that is limited to the surface. Alternatively, these methodologies require transport of the laser beam to a highly specific area, in a highly limiting fashion, by way of an invasive intrusion, for example with an optical fiber or other laser guiding device.

Thus, for example, no previous solutions of AMD have been able to bleach the subretinal pigments that are the cause of this disease without collateral damage to the overlying retina. This is the case even though higher order laser effects are known in microscopic analysis and can interrogate specific layers with the characteristics required (see analysis of T. Wilson and C. J. R. Sheppard, Theory and Practice of Scanning Optical Microscopy Academic Press, New York 1984). These effects could not be effectively be used in therapy without the controlled in vivo characterization of parameters required for ultralow to zero collateral damage to the surrounding tissue. Thus, no such treatments have even been considered because of these problems (see H. Sun and J. Nathans, "The Challenge of Macular Degeneration," Scientific American, October 2001, p 61).

In addition to AMD, fungal infections have remained essentially impossible to eradicate in places like the region under the nails of the feet, because of the lack of accurate parameterization for the highly specific, highly controlled treatments that are required.

Furthermore, no previous invention or report had shown site specific, prolonged expression of genetic material administration in vivo with any type of laser-related methodology (see for example Tao et al PNAS (USA) 84:4180-4, 1987; Kurata and Ikawa Cell Struct Funct 11:205-7, 1986; Paulombo et al J Photochem Photobiol 36:41-6, 1996).

Laser-related methodologies have been disclosed for example in U.S. Pat. No. 6,251,099, which teaches the use of pulsed laser light in order to generate "impulse transients" for delivering substances through the skin. These impulse transients generate transient increases in the permeability of epithelial tissue, thereby enabling the substances to penetrate. However, the laser light is not described as being useful for administering substances and/or performing therapeutic treatments within intermediate tissue layers, as would be required for the treatment of AMD, for example.

U.S. Pat. No. 4,775,361 discloses a method for administering a therapeutic substance through the skin of a patient, by using a pulsed laser beam of controlled wavelength, pulse length, pulse energy, pulse number and pulse repetition rate, sufficient to ablate the stratum corneum (outer layer of the skin) without damaging the epidermis. The therapeutic substance is then applied to the area of skin with the ablated stratum corneum. However, the disclosure still requires destruction of a portion of tissue. Therefore, the disclosed device of U.S. Pat. No. 4,775,361 could not be used for treatment of AMD, as it would damage retinal tissue above the area to be treated.

U.S. Pat. No. 5,713,845 describes the use of laser to force drugs into the skin, for example on small graphite particles which act as an explosive absorber of light energy. The laser beam is transmitted in very short pulses, which cause small explosions that force the drug through the skin. Clearly, the disclosed system is not suitable for applications in which the laser has to penetrate some distance of tissue before reaching the tissue to be treated. Thus, the disclosed system could not be used to treat AMD, as it would also damage retinal tissue above the area to be treated.

Gene therapy itself faces many obstacles before it will become a widely available method of treatment. A major obstacle in applying theoretical and experimental gene therapy methods into clinical practice is the current complexity of gene delivery systems. Viral vectors for gene delivery have shown great promise in relation to their efficiency, longevity and targeting capacities (1). The use of retroviral vectors for gene delivery in correcting genetic maladies in children was implemented clinically and initially, showed promise (2, 3). However, a number of unresolved issues concerning viral gene delivery remain. These include, among others: the potential for anti-viral immunological reactions; risk for development of malignant phenotypes associated with improper gene integration; size limitations on vector capacity; and challenges in the production of Good Manufacturing Practice (GMP) grade genetic material free of replication-competent viruses, that is suitable for clinical use (4). Hence, attention has focused on the use of non-viral methods of gene delivery such as cationic liposomes that transport foreign genes through cell membranes, or "naked DNA" constructs in which the desired gene is incorporated into a plasmid that may be injected directly into muscle or other tissues (5, 6). This latter technique requires physical methods such as electroporation (EP), that transiently fenestrate the cellular and nuclear membranes (5, 6). However, the in vivo efficiency of these methods is often low. Recent modifications such as the use of ultrasound energy (7) or microfabricated devices (8) to enhance naked DNA uptake in muscle or the dermis, respectively, have been successful in specific cases. Other potentially powerful genetic therapy tools include: anti-sense nucleotides, ribozymes, intron I and II based nucleic acids, and therapeutic small interference RNA (RNAi), some of which have been assessed in animal models and in preliminary clinical trials (9, 10). However, most methods still face significant obstacles in their specific applications due to gene delivery problems. One of these is that in vivo electroporation of naked DNA into large animals, even with enhancing delivery molecules such as polyethylenimine, will likely require a high-energy pulse>500 V (11) that while theoretically efficient for gene transduction, would not be practical as it would create considerable risk for local tissue injury (burn) or other deleterious effects (cardiac arrest).

SUMMARY OF THE INVENTION

The present invention is of a highly controlled and precise system, device and method for tissue and cellular alteration and treatment below or at surfaces with a laser. The present invention is characterized by ultra low levels of collateral damage. The operation of the present invention is based on spectrally confining the nature of the interaction that results when a laser spot is created with a large fluence, or large intensity per square unit of area, in a short time at a targeted tissue.

The present invention provides a non-invasive treatment at any level in the tissue based on the spectral confinement of laser tissue interaction with critical diagnostic methods for characterizing the penetration, the level of laser power, the frequency of the laser light, the focus of the beam and the determination of the precise three-dimensional area to be treated. This is a preferred and important component of the invention that allows for characterizing the in vivo conditions of the laser tissue alteration and for defining the parameters that are needed to achieve the desired effects. Preferably, this characterization is based on the use of higher order laser poration of specific tissue layers with the site specific administration of nucleic acids in the form of RNA and DNA, and/or other macromolecules and/or particles and/or other pharmacological compositions. The latter compositions can include material that is associated with a specific disease state and which can be placed at the specific depth of the tissue being targeted. Since the present invention also includes an accurate determination of the laser levels that allow for viability, functional assays of tissue and cellular systems are also optionally and preferably provided. Although specific combinations of disease, higher order laser effects and diagnostic methods for tissue viability are chosen for the target applications described in this invention, other emulations or other combinations can be conceived, based on this principle of defined diagnostics to achieve ultralow to zero collateral damage in underlying laser tissue interactions, for any type of disease and not limited only to those diseases and/or pathological conditions directly addressed herein.

For example, optionally and preferably, at least one parameter is monitored in vivo to permit a specific pathological condition to be treated according to the present invention, in which the specific pathological condition features a particular molecular species, according to an effect of the particular molecular species determined after an injection into a similar live tissue.

The combination of defined diagnostics enables higher order laser effects to be applied to these disease states for the first time. Thus, the present invention has taken higher order laser effects that have been previously known (T. Wilson and C. J. R. Sheppard, Theory and Practice of Scanning Optical Microscopy (Academic Press, New York 1984)), and have enabled these effects to be applied to diseases that require ultra low to zero collateral damage through defined methods of characterization and control developed in the present invention. The present invention also does not need either an external highlighting agent or an invasive beam delivery system for the laser treatment or alteration of tissue at or below the surface.

The present invention is applicable to a large number of therapeutic and other problems, including but not limited to, the administration of genetic material such as DNA, RNA, or any other such material, the administration of any biopharmaceutical composition other than DNA or RNA, treatment of conditions such as AMD, and other age and non-age related degenerative diseases, chronic infectious disease, autoimmune diseases, vaccinations and malignancies, and fungal and other infections.

The present invention may optionally and preferably be used to treat infections that require a total destruction of tissue without affecting the overlying and underlying tissue. An example is a fungal infection in an underlying tissue layer that is preferably be removed without damaging the overlying tissue. A specific case is fungal infection under cutaneous tissue like the nail of the foot that has to be destroyed without damaging the overlying or underlying tissue.

The present invention may also optionally and preferably be used for separation of cells (with and without genetic markers), and for diagnostics, with or without dye molecules.

Hereinafter, the term "ultra-low collateral damage" refers to collateral damage which still permits surrounding cells to maintain viability, wherein such viability can be determined according to appropriate controls for demonstrating cellular viability.

BRIEF DESCRIPTION OF THE DRAWINGS

The foregoing and other objects, aspects and advantages will be better understood from the following detailed description of a preferred embodiment of the invention with reference to the drawings, wherein:

FIG. 10. To assess the level of muscle injury the CPK serum enzyme marker for myofiber lysis was determined. CPK in the serum of the mice collected 2 hours post-injection. Normal mice, mice injected with the plasmid only and mice injected with the plasmid were stimulated 30 seconds later with either the laser beam or electroporation. As seen, the level of CPK activity with the laser beam method was 6 fold lower compared to electroporation. It is interesting to note that despite repetition of the experiment, CPK serum activity levels in the laser beam treated mice were found to be lower that that of the normal and plasmid-injected-only mice.

FIG. 13. The bleaching of fluorescein under the retina of the live eye of a rat. The frames on the left of this figure show a view of the retina with a slit lamp and its associated illumination. The arrow indicates a region of multiphoton fluorescence excited by the ultrashort laser. The frames on the right are of this spot of fluorescence and its time dependent photobleaching which is easier to delineate without the presence of the slit lamp illumination. Nonetheless, even with slit lamp illumination the photobleaching is also clearly visible. Each frame corresponds to a point in the graph shown in FIG. 14.

DESCRIPTION OF PREFERRED EMBODIMENTS

Figure 1:
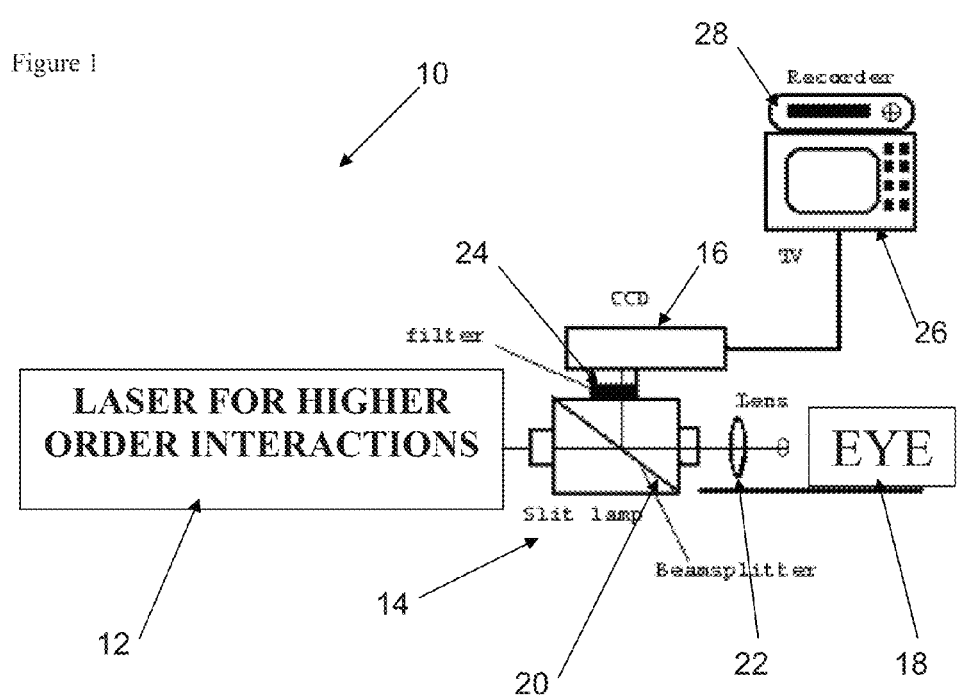
FIG. 1: The system used in the invention to accomplish the tissue alteration and gene transduction based characterization is shown. This instrument is just one example of the geometry of the interaction with the tissue. Other tissue interaction geometries could include transmission of the laser for higher order interactions through the tissue. This is required for such applications as second or third order effects for functional diagnosis of tissues and cells in which specific gene expression occurs as a result of the protocols described herein.

The present invention is of a highly controlled and precise system, device and method for tissue and cellular alteration and treatment below or at surfaces with a laser. The present invention is characterized by ultra low levels of collateral damage. The operation of the present invention is based on spectrally confining the interaction between laser energy and a targeted tissue while choosing a physiologically relevant parameter to determine the power levels that can achieve a level of collateral damage that is consistent with effective function at the cellular level of the targeted tissue.

The approach is based on-using to advantage the higher order terms of the polarizability tensor that describes the interaction of light with matter to limit the laser tissue interaction to a particular region of tissue. This polarizability tensor, which defines the interaction between light and matter, consists of a series of terms to mathematically approximate the polarizability of the material with the light. Whereas the first term in this series describes conventional absorption and scattering of laser light, the higher order terms are preferably used for performing the present invention.

For the higher order terms discussed above to have an appreciable effect, the number of photons per square area per time has to be very high. This can be arranged using a lens that creates a beam shape in which there is low fluence at every point other than at the focus. Non-linear interactions occur when more than one identical photon occupies the same space at the same time. The level of fluence at which light has the non-linear interactions depends on the ultrashort nature of the pulse; the shorter the pulse, the higher the probability that more than one identical photon will appear in exactly the same area or location.

Also, these higher order terms permit the effect of the geometrical focusing to be increased by the nature of the higher order phenomena being used to alter the tissue. In addition, the higher order interaction of the laser with the tissue permits infrared radiation to be employed and this further reduces the absorption of tissue in regions that are above and below the selected region of interest. Finally, if the laser is tunable then not only is the infrared nature of the radiation used to advantage but also the wavelength of the infrared radiation can be chosen so that the higher order interactions can be accomplished with maximal effect.

Although specific examples of different types of lasers and laser systems are described below, the present invention is generally operable with any type of laser or laser system having suitable characteristics. These characteristics may also depend upon the type of treatment, and/or the type of tissue being treated. For example, the present invention is optionally and preferably operable with any pulsed laser. The particular pulsed laser is preferably selected according to particular situations; for example, the pulse width is optionally and preferably optimized according to the type of treatment and/or tissue.

Optionally and preferably, "ultrafast" lasers with "ultrashort" pulse durations are used for the present invention. The nature of the ultrashort laser pulses is defined by the resolution that is required by the depth of penetration; the present invention is operable with femtosecond lasers as described below in the seconds, but may also optionally be operable with picosecond and ultrasecond lasers, for example.

The range of operating power (in watts) depends on the pulse width and repetition rate, which is preferably optimized for specific tissues and/or treatments; the shorter the pulse, the lower the amount of collateral damage that is caused, and the higher the resolution in depth of penetration, in terms of targeting specific tissues.

The range of suitable operating wavelengths depends upon the depth of penetration that is required. For example, minimal water absorption occurs at about 1.5 microns; for highly aqueous tissues, better penetration is achieved at wavelengths closer to 1.5 microns. Nonetheless, such parameters are preferably adjusted relative to the non-linear methodology that is chosen for tissue intervention. For example, even though the depth of penetration is highest at 1.5 microns in an aqueous medium, the efficacy of this wavelength for AMD is very low; hence the maximal bleaching of the drusen droplet can only occur at much shorter wavelengths, such as 800 nm or 0.8 microns. Thus in such a clinical situation, where depth of penetration is not detrimentally mediated by the tissue in front of the drusen droplets, a wavelength of 800 nm would be preferred.

A suitable beam diameter (or range of beam diameters) is preferably chosen according to the dimensions of the tissue that is to be treated. Appropriate lens combinations which allow the light to be focused are determined according to the numerical aperture, magnification and working distance of the lens, which are preferably chosen as appropriate for the size of tissue being treated, and the depth of that tissue.

These different parameters are preferably determined in order to characterize the laser beam according to a plurality of parameters for permitting the second order term of the higher order expression of the polarizability tensor for describing the interaction of light with matter to be used to perform second harmonic generation substantially without tissue alteration.

Characterization of the Laser Tissue Interaction for Tissue Alteration for Disease Treatment Age related macular degeneration (AMD) currently is not treatable with regard to the root cause of the disease. Even though lasers have been applied in ophthalmology for many decades, the application of the laser to this disease has not been possible, since the disease originates from the development of deposits of pigment in retinal pigment epithelium (RPE) cells, slowly killing them and causing the neighboring light sensitive photoreceptor cells to die. An important pigment deposit is the pigment known as A2E ("Isolation and one-step preparation of A2E and iso-A2E, fluorophores from human retinal pigment epithelium," *Proc. Natl. Acad. Sci. USA* 95, 14609 (1998)).

In fact the total lack of cure or effective retardation of AMD is evidenced by a review recently published from a center of AMD research at Johns Hopkins University by one of the leaders in this field, Jeremy Nathans (see H. Sun and J. Nathans, "The Challenge of Macular Degeneration," Scientific American, October 2001, p 61). In essence no approach with lasers to cure or to effectively retard this disease by targeting the pigments that result in the disease has been successful, and the only approach that has a palliative effect is photodynamic therapy for the retardation of blood vessel growth in the Bruch's membrane, which is a treatment for a symptom or response of the disease rather than the cause of the disease.

FIG. 1 shows an exemplary system 10 according to the present invention for treating AMD. A laser 12 that can be used to cause higher order laser tissue interactions is shown. Laser 12 is preferably an ultrafast laser, also termed herein as an ultrashort laser, which may be for example a near-infrared laser having time durations of $\sim 60 \times 10^{-15}$ sec, which can be focused to a point below a surface and can be made to affect only the point of focus, and not the overlying or underlying material through which the laser beam is transmitted:

Optionally and more preferably, laser 12 is a pulsed laser which has the ultrashort pulse duration of ($\sim 60 \times 10^{-5}$ secs). Such an ultrashort pulse (for example, a femtosecond laser) leads to interactions of light with matter that are highly non-linear. This means that the light that is focused by a lens 22 above and below the plane of focus does not have a high enough fluence (intensity per square cm) to result in these non-linear interactions, i.e. interactions in which the density of photons is high enough so that more than one photon or packet is found at the same point in the sample at the same time. Only in the plane of focus of lens 22 is the density of photons high enough to allow this to happen. As a result of such a non-linear event, highly localized absorptions and emissions are produced.

Laser 12 is preferably focused by appropriate optics, which in the case of AMD treatment preferably includes a slit lamp 14 to microscopically view the organ (shown as an eye 18) and lens 22 that focuses light with the appropriate fluence for the higher order interactions in the layer of tissue that is to be altered. In all cases, the organ is located beyond lens 22. Slit lamp 14 preferably also includes a beamsplitter 20.

Appropriate lens combinations are preferably used to form a spot with a resolution of several microns behind the retina without the touching the overlying retina. Next, preferably a filter 24 filters the light received by a CCD camera 16. The information may optionally be displayed by a television system 26 and/or recorded by a recorder 28, for the purpose of live, "real time" monitoring of the process.

The in vivo diagnostic test is an optional but preferred part of this invention, in order to verify the power levels that do not damage the overlying retina. Such in vivo diagnostic tests can be one of several types, of which two non-limiting examples are described below. A first example is the online measurement of electrophysiological parameters in an animal model in which the newly synthesized pigment A2E has been injected behind the retina. A second example is the gene expression assay as described below.

Without wishing to be limited to a single hypothesis, it is probable that the lack of the application of this approach was the lack of understanding of how optics could accomplish this in such a complicated tissue, even with such a laser, with such a large distance from the entrance of the eye to the tissue in question. In addition, a critical aspect has been the inability to define the associated physiologically relevant measurements developed with regard to the present invention to determine the power levels that would permit the essential ultra low collateral damage. This is in spite of the fact that higher order phenomena have been known for a long time in microscopy (T. Wilson and C. J. R. Sheppard, Theory and Practice of Scanning Optical Microscopy (Academic Press, New York 1984)).

Thus, the invention includes a concept of treatment which is based upon the combination of appropriate optical techniques with lasers that could generate higher order interactions in tissue, and which have the ability to bleach pigments such as the newly synthesized A2E without touching the overlying retina as defined by either physiological or genetic tests.

In terms of the first example of a physiological test noted above, optionally and more preferably, the present invention includes injecting A2E pigment into the tissue behind the retina of an animal model, in order to set the parameters necessary for the accurate bleaching of this pigment with higher order effects, while minimizing damage to the overlying retina as determined by simultaneous electrophysiological measurements.

Alternately, genetic expression, as described below, can be used as a monitor of the surrounding tissues' ability to remain viable and this can be monitored relative to the power levels that can bleach the newly synthesized molecule A2E.

The same or similar arrangement can optionally and more preferably be used for fungal infections with appropriate alterations of the arrangement and treatment according to the organ being modified, more preferably by altering the optical components described in FIG. 1 as required to cause this modification. The gene insertion procedure described below can be used to set the exact thresholds of the higher order laser effects in this geometry that will not affect the surrounding tissue.

The same or similar arrangement can also optionally and more preferably be used for gene insertion, again with the appropriate alterations, particularly with regard to the energy requirements of the laser so that the higher order phenomena cause poration of the cells in the layer of tissue being considered, with minimal or no collateral damage to surrounding tissue.

The ability to insert genes that can be expressed in specific tissue layers is a preferred embodiment of this invention since the monitoring of gene activity may optionally be used for characterization of the layer of tissue being altered by the laser, as well as for determination of the laser intensities required for keeping the cells in the appropriate layer alive after laser treatment. Thus, the appropriate energy densities are more preferably achieved in a more precise and controlled manner after this critical characterization.

Characterization of the Laser Tissue Interaction for Gene Transduction

One important and preferred aspect of the present invention is the characterization and control of the laser treatment process, for maintaining viability after the interaction with the laser in a specific underlying layer of tissue. The process of gene transduction may optionally be used to monitor and define the characteristics of this laser tissue interaction for other types of applications, in addition to gene therapy.

One of the major limitations in translating the concept of gene therapy into a routinely used therapeutic approach is the low efficiency of gene delivery and transduction of target cells. To overcome these bottlenecks, in recent years a spectrum of new delivery and gene transduction methods were developed and assessed in a variety of animal models. In general three approaches were developed to enable gene transduction into target cells: the use of viral vectors; cell therapy with or without genetic manipulations; and non-viral gene therapy.

The major advantage of using viral vectors is the relatively efficient transduction efficiency and the possibility for conducting specific targeting in specific cases. However, viral vectors harbor major limitations related to the expression of foreign genes, inducing an immune response or enabling prolonged expression. To meet these objectives, new modified viral vectors were developed, one of which is the adenoviral vector. The helper dependent adenoviral vector is a gutless virus, which infects most human cells through the CAR receptor. Due to the fact that the gutless vector doses not express any viral genes, the immune response against infected cells is very low, enabling prolonged expression. However, construction of such vectors is very laborious and needs specific expertise. In addition, the effect of repeated administration of such vectors for a long period of time was not assessed until now.

An alternative viral vector transduction system recently developed is the HIV based vectors. Here again there are significant advantages with major limitations. The most significant advantage of the latest generation of the HIV vectors is their large genome capacity, as almost all accessory genes have been deleted. Following transduction, these vectors enable stable integration of the transgene into the host genome. However, there are still a number of unresolved limitations. Until now, generating high titers of the viral vector has proven to be difficult. For example, there are batch to batch variations due to the fact that stable cell lines are not yet available, and there are also safety issues related to this type of vector.

Other than the adenoviral and the HIV vectors, additional important advances were reported with the AAV vector as well as with other viral vectors including the SV40, FIV and other new approaches. However, for each of these new viral vectors there are significant limitations hampering their progress application to enter clinical use.

The alternative approach to viral vectors in gene transduction is naked DNA delivery for transgene expression. The major advantage of naked DNA gene therapy approach is its simple production process and low or negligible immune response other than in cases where DNA is injected with specific adjuvant to induce an immune response in the case naked DNA is used for vaccination. The use of naked DNA is problematic due to low transfection efficacy of currently available methods, including liposomes and other non-immunogenic compounds such as dextran which are mixed with the DNA. In addition, targeting to specific sites is a barrier.

To overcome this barrier, DNA can be injected to reachable organs such as the muscle, which was found to be a sufficient producer of protein as shown in small animals following muscle electroporation of DNA. However, naked DNA electroporation, although an efficient gene transduction approach, is poorly reproducible in large animals. The efficiency of electroporation in large animals is very low. In addition, electroporation, which is in practice an electrical shock, could be unsafe and hazardous for patients, particularly since much higher voltages (>500 V) are required in larger animals, and hence, in practice would be hazardous for human patients, as it could cause serious tissue damage.

Previous reports suggested that various methods, which probably disrupt the cellular membrane transiently, could support DNA entrance into living cells. Between 1993 and 2001 a single group had received patents (U.S. Pat. Nos. 5,272,072; 5,330,467; 5,586,982; 6,071,276 and 6,190,380) for the development of a laser catheter to induce genetic material through introducing a laser catheter inside blood vessels or by direct application over cells. Such an approach could be applicable for specific cases but would need additional manipulations for operation such as an angiographic monitoring facility and other sophisticated devices.

The present invention, by contrast, enables the use of a different laser beam device, which does not require direct contact with the target tissue. Such an approach enables the laser to be applied externally, at a location which may be distant from the target tissue itself. To this end, the present invention preferably includes a laser beam source which is located outside of the body to support muscle gene transduction.

The potential advantage of higher order laser interactions is that they include energy that is directed and targeted at a specific layer of tissue, and which can be effectively used for gene transduction. As described in greater detail below, the laser treatment of the present invention is suitable for the delivery of genetic material by using an energy pulse from a laser, which in the examples below was a femtosecond titanium sapphire near-infrared laser. This laser system has the capacity to focus energy at a specific level in the muscle tissue below the surface of the skin. As these ultrashort laser pulses are in the near-infrared region, there is less scattering by the tissue and thus, deeper penetration. Also, by appropriate optical manipulation, i.e. the use of a long working distance lens, and also by using a lens having a high numerical aperture, maximal influence of the laser in the targeted tissue is achievable with high resolution and minimal collateral tissue damage.

Without wishing to be limited by a single hypothesis, it would appear that the cells in the laser-illuminated region undergo gentle poration, which transiently increases their membrane permeability without permanent damage. Although the examples below demonstrate that laser beam gene transduction according to the present invention may optionally be used to deliver naked DNA constructs, such as a plasmid expressing the murine erythropoietin (mEPO) gene, resulting in high and persistent mEPO expression with negligible tissue damage, in fact the present invention is expected to be useful for the introduction of many different types of macromolecules and/or particles into cells. Also, the present invention is expected to be applicable for gene delivery into a variety of target tissues. Further, it is anticipated that the present invention provides a safer and a more effective method than the "conventional" electroporation techniques for gene delivery in larger animals and humans due to the larger available muscle tissue mass over which the laser energy can be applied, and the avoidance of electrical shocks.

In terms of suitable parameters for introducing genetic material, the genetic material itself may optionally be used in any suitable form for gene therapy. For example, different types of DNA constructs that could be used for gene therapy may also optionally be used for gene transduction with the present invention. Non-limiting illustrative examples of promoters that are suitable for use with the present invention include E1a, CMV and SV40 for non-tissue specific expression; Desmin, CK and CAG for specific muscle expression. The genetic material may also optionally be used as naked DNA and/or naked viral vectors, and/or with various types of suitable carriers.

Furthermore, the present invention is not limited to the introduction of DNA molecules into cells, as any type of genetic material, such as RNA for example, could optionally be used. Also, many different types of macromolecules may also optionally be introduced into cells with the laser treatment of the present invention, such as proteins, lipids, and polysaccharides for example. Also optionally, various suitable carriers may also be used with these macromolecules. Also, optionally different combinations of macromolecules could be used, for example to encapsulate macromolecules such as RNA, DNA and/or proteins for example, with other macromolecules such as lipids for example, to provide a carrier. The resultant macromolecular structure may also optionally be virus-like in terms of the particle structure.

Example 1

Gene Transduction with Higher Order Laser Effects

The device and system of the present invention was tested according to the method of the present invention, for determining the efficacy thereof for gene transduction.

The objective of these experiments was to assess the possibility of transducing a DNA expression cassette into muscle cells by applying an external laser beam source after naked DNA administration.

Methods

Ultrashort (Femtosecond) Laser Apparatus

The interaction of the laser beam with the tissue depends on laser power, pulse duration, surface area illuminated, and the depth and the nature of focal parameters of the laser beam at the layer of tissue being targeted. For these experiments, a Coherent Radiation Mira Titanium Saphire mode-locked laser emitting 200 fsec pulses with a 76 MHz repetition rate, was pumped by an argon ion laser (Coherent, Innova 200) that was operated at 12 watts in a multi-line mode. This particular laser is an example of a femtosecond laser, but may be more generally considered as a preferred but non-limiting example of an ultrashort laser for use with the present invention. It should also be noted that optionally, the method of pumping a pulsed laser could be performed according to any of the generally accepted methodologies, including but not limited to, single or multi-line optical pumping, electrical pumping or chemical pumping.

Figure 2:
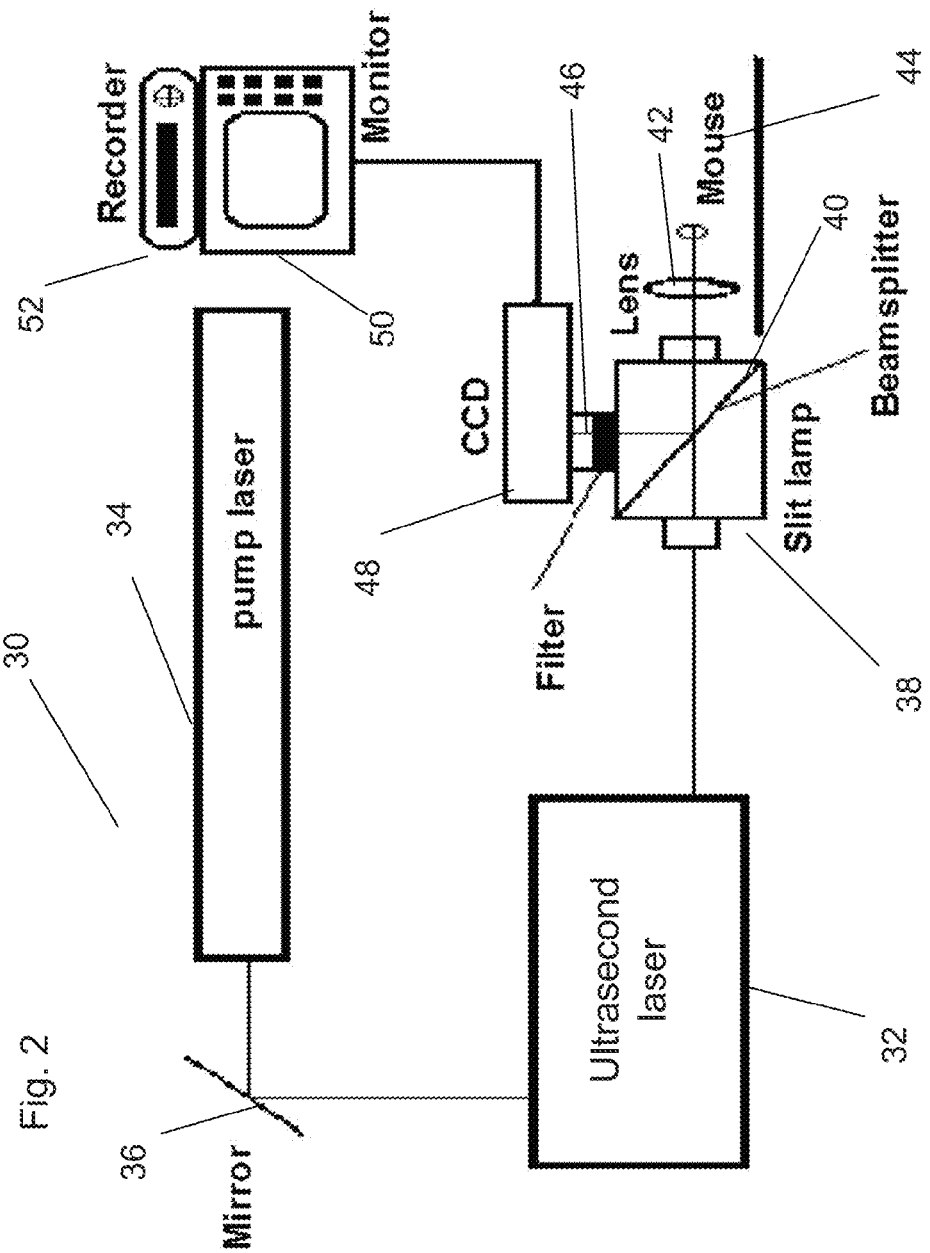
FIG. 2. Exemplary laser apparatus for gene therapy according to the present invention. A femtosecond infrared mode-locked Ti:Sapphire laser (Coherent, Mira 900) was used as an illumination source. It was pumped by an argon ion laser (Coherent, Innova 200) that was operated at 12 watt in a multi-line mode. The operating wavelength was 780 nm, the pulse frequency was 76 MHz, and the pulse duration was about 200 fsec. The laser beam was transmitted via an inverted microscope (Zeiss, Axiovert 135) and focused by ×50 N.A 0.5 objective (Zeiss) on the sample.

For this example, the operating wavelength of the laser was 780 nm. The laser beam was transmitted via an inverted microscope (Zeiss, Axiovert 135) and focused by ×50 N.A 0.5 objective (Zeiss) onto an anaesthetized animal that was placed securely on the microscope stage. The tissue was irradiated at depths 1, 2 or 3 mm under the skin using a beam scanning system used in confocal microscopy over a tissue region (95 micro-$m^2$) which had been injected 30 seconds before the irradiation (see FIG. 2). The dwell time at each of approximately 250,000 pixels in the scan was tens of microseconds with the entire scan time being 5-20 seconds. The laser powers that were used varied between 10 to 30 mwatt with an optimum (for these experimental conditions) being about 20 mwatts (FIG. 2). It should be noted that these parameters are illustrative only and are not intending to be limited in any way.

As shown in more detail with regard to FIG. 2, a system 30 was used for the experiments. It should be noted that system 30 shows an exemplary, non-limiting configuration of the present invention. System 30 features a laser 32, which is preferably an ultrashort laser, such as a femtosecond laser for example. For the example below but without any intention of being limiting, laser 32 was a femtosecond Ti:Sapphire laser. Laser 32 may be the type of laser which is activated or "pumped" by another laser, shown as a pump laser 34. For the example below but without any intention of being limiting, pump laser 34 was an argon ion pump laser. The beam from pump laser 34 was bent with a mirror 36 as shown, as is well known in the art.

The beam from laser 32 was then transmitted to a slit lamp 38, featuring a beamsplitter 40. The beam was focused by the optics of slit lamp 38 and also preferably by a lens 42, onto a sample, shown herein as a mouse 44 for the purposes of illustration only and without any intention of being limiting.

A filter 46, for this example a green filter, filtered light being transmitted to a CCD camera 48 and hence to a monitor 50 and/or a recorder 52, for the purpose of live "real time" monitoring of the process.

Electroporation

Caliper electrodes were used for EP (BTX Caliper electrode Model 384 (1 $cm^2$). Before EP, a conductive gel was applied to the shaved skin on either side of the marked injection point, and the calipers were closed to a gap of about 4 mm, so that the muscle was between the electrode plate extensions and electrical contact with the skin was maximized. Consecutive square-wave electrical pulses were administered using a BTX eCM 2001 pulse generator (BTX, San Diego, Calif.) at an interval of one-second between pulses. The EP settings were at a chosen mode of LV (500 v/99 msec). The voltage was set at 100 V. The desired field strength was 200 v/cm. The setting for the pulse length was 20 msec, and 4 pulses were given, after which the polarity was reversed. A total of 16 pulses were given.

Intramuscular Injections and Animals

Female BALB/c mice (obtained from Harlan Laboratories, Jerusalem, Israel), aged 4-6 weeks, were anesthetized by intraperitoneal injection (IP) of 0.2 ml of 4% chloral hydrate/saline solution (Fluka-Sigma, Israel cat no 23100). The point of injection was marked and 10 or 15 micro-g of plasmids pLNC/Luc, or pcDNA.3/Luc or pcDNA.3mepo in a volume of 30 micro-1 of 0.9% NaCl, were administered into the tibia cranial muscle using a 27½-gauge needle and a 0.5 cc insulin syringe. The Institutional Animal Welfare Committee approved all animal experiments. All animals were given humane care in compliance with institutional guidelines. All animals drank tap water and were fed rat chow ad libitum. Animals were kept with a 12 h light-dark cycle at constant temperature and humidity.

Plasmid Vectors

The pLNC/Luc was constructed by introducing the firefly luciferase gene (luc) downstream to the CMV promoter in the plasmid vector pLNC. The plasmid pcDNA.3mepo containing the mouse erythropoietin (Epo) ORF was provided. It was constructed by inserting the mouse Epo cDNA into a unique BamH1 site between the human CMV immediate early promoter/enhancer and a 3'-flanking sequence of the bovine growth hormone gene polyadenylation signal from the pcDNA.3 expression vector. This mouse Epo cDNA contained the entire 630-base pair. (630-bp) Epo-coding sequence. The empty pcDNA.3 backbone plasmid was used as a control. Plasmids were amplified in *Escherichia coli* JM109, and prepared with a Qiagen Endo-Free plasmid Giga kit (Qiagen GmbH, Germany).

Blood Sampling and Serum Biochemical Analysis

Blood samples were collected from the retro-orbital plexus from anesthetized animals. Blood samples were obtained on day −2 (preinjection time point) and on the indicated times following in vivo electroporation (EP) or laser beam gene therapy (LBGT). For the measurement of muscle damage following laser beam gene therapy application, or electroporation (EP), creatine phosphokinase (CPK) levels were measured in the serum of mice. For the assessment of the effect of transduced mEPO genes, blood hematocrit (Hct) was measured by using a Coulter STKS electronic counter for standard analysis.

In Vivo Imaging and Quantification of Gene Expression.

For the detection and quantification of gene expression continuously in the live animals the CCCD imaging system as described in Honigman, A., Zeira, E., Ohana, P., Abramovitz, R., Tavor, E., Bar, I., Zilberman, Y., Rabinovsky, R., Gazit, D., Joseph, A., Panet, A., Shai, E., Palmon, A., Laster, M., and Galun, E. (2001). Imaging transgene expression in live animals. *Mol Ther* 4: 239-249, hereby incorporated by reference as if fully set forth herein. In brief, the Roper Chemiluminescence Imaging System was used. This system contains the cooled CCCD model LN/CCD-1300EB equipped with ST-133 controller and a 50 mm Nikon lens (Roper scientific, Princeton instrument, Trenton, N.J.). In all experiments mice were anesthetized before light detection, and 5 minutes before monitoring light emission, the animals were injected i.p. with Beetle luciferin (Promega Corp., Madison, Wis.) in PBS at 126 mg/kg body weight. The animals were placed in a dark box, supplemented with a controlled light in order to take pictures of the background image. The light measurements were taken at the same conditions, including time (2 min) and distance of lenses from the mice.

Histology and Immunohistochemistry

For routine histological analysis formalin fixed paraffin embedded muscle samples were cut into sections 4 micro-m in thickness, deparaffinized in xylene and rehydrated through a series of decreasing concentrations of ethanol. Sections were stained with hematoxylin and eosin.

For immunochemical detection of luciferase (performed as described in Lavon, I., Goldberg, I., Amit, S., Landsman, L., Jung, S., Tsuberi, B. Z., Barshack, I., Kopolovic, J., Galun, E., Bujard, H., and Ben-Neriah, Y. (2000). High susceptibility to bacterial infection, but no liver dysfunction, in mice compromised for hepatocyte NF-kappaB activation. *Nat Med* 6: 573-577, hereby incorporated by reference as if fully set forth herein), paraffin-embedded sections were pretreated by incubation in 0.01 M citrate buffer and heated in a microwave twice for 5 min. Samples were then incubated for 60 min at room temperature with rabbit polyclonal antibodies against luciferase (1:100 dilution; Cortex Biochem, San Leandro, Calif.), washed and incubated with biotin-conjugated goat antibody anti-rabbit (1:100 dilution; Jackson Immunoresearch, West Grove, Pa.). Afterward, the samples were labeled with peroxidase-conjugated streptavidin and detected using 3-amino-9-ethyl carbazole substrate.

For the detection of β-galactosidase gene expression, 6 days after DNA injection of DNA, tibial muscles were excised from all treatment groups and β-galactosidase activity was measured using the whole-mount method as previously described (as described in Duguez, S., Feasson, L., Denis, C., and Freyssenet, D. (2002). Mitochondrial biogenesis during skeletal muscle regeneration. *Am J Physiol Endocrinol Metab* 282: E802-809, hereby incorporated by reference as if fully set forth herein). The 5-bromo-4-chloro-3-indolyl β-D-galactoside (x-gal) stained tissues were digitally photographed. Subsequently, the tissues were paraffin embedded and 5 micro-m sections were postfixed by incubating the sections at 4° C. for 1 h in PBS/1% gluteraldehyde. The sections were then washed 3 times in cold PBS containing 2 mM $MgCl_2$, stained with a solution consisting of 1 mg/mL of x-gal solution in PBS, 5 mM $K_3Fe(CN)_6$, 5 mM $K_4Fe(CN)_6$, and incubated at 37° C. overnight.

Image analysis was performed using a light microscope at 40× magnification. To detect green fluorescence protein (GFP) gene expression, the muscles were frozen in OCT tissue embedding medium and sectioned (6 micro-m) with a cryostat. Sections were placed on polylysine-coated slides, fixed in acetone for 30 seconds and GFP expression was observed by direct fluorescence microscopy using a Nikon eclipse E600 microscope and photographed with a digital camera (as described in Blair-Parks, K., Weston, B. C., and Dean, D. A. (2002). High-level gene transfer to the cornea using electroporation. *J Gene Med* 4: 92-100, hereby incorporated by reference as if fully set forth herein).

Results

Part 1—Control Study

First the effect of naked DNA injection (negative control) was assessed in the experimental model system, in comparison with naked DNA injected followed by electroporation (positive control).

The animal model featured BALB/c mice (female, 4-7 week old) which received a pLNC/luc construct injected into the muscle. These experiments were conducted with mice in groups of three mice, and were performed between two to three times repeatedly. The pLNC/luc DNA vector has a backbone of a retroviral vector. The luc gene was derived from the CMV promoter and the construct also included the Neo resistance gene. Fifteen micrograms of plasmid pLNC/Luc, in a volume of 30 microliters of 0.9% NaCl was injected into the tibia cranial muscle of anesthetized BALB/c mice. The leg skin was shaved and a conductive gel was applied in order to ensure the electrical contact. Thirty seconds after the DNA injection, electric pulses were applied using plate electrodes at each side of the leg. The leg skin was shaved and a conductive gel was applied in order to ensure the electrical contact. A BTX electroporator (ECM 2001, BMX, San Diego, Calif.) was used to deliver pulses for 1-99 ms. The electroporation settings were: 100V for 20 ms for a total of 16 pulses. The results of this experiment are shown in FIG. 3.

Figure 3:
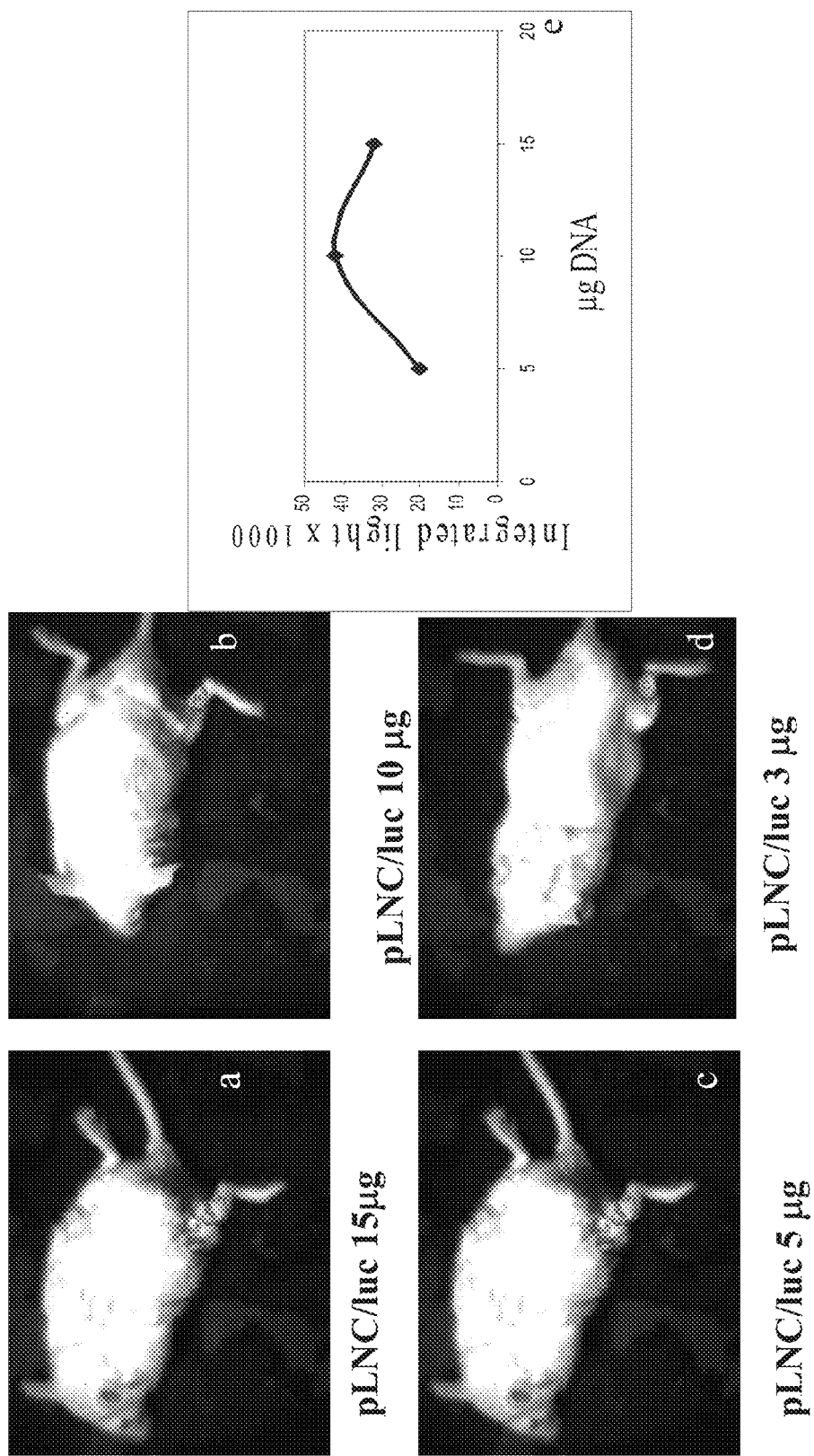
FIG. 3. Luc expression from the leg muscle of mice following injection and electroporation of naked pLNC/Luc DNA as control experiments. 3, 5, 10 and 15 μg of pLNC/Luc were injected followed by electroporation, to the leg muscle of BALB/c mice (a-d). Quantification of the light readings is presented in (e). The contra-lateral leg is always injected with the same dose of DNA without electroporation.

Briefly, FIG. 3 shows Luc expression from the leg muscle of mice following injection and electroporation of naked pLNC/Luc DNA as control experiments. As shown in FIG. 3, 3, 5, 10 and 15 μg of pLNC/Luc were injected followed by electroporation, to the leg muscle of BALB/c mice FIG. 3a-d). Quantification of the light readings is presented in FIG. 3e). The contra-lateral leg was always injected with the same dose of DNA without electroporation.

The conclusion from this experiment, which is in the same line as reported by other groups in recent publications, is that naked DNA alone is not sufficient to induce gene expression and an additional DNA cellular entrance facilitator is needed. Due to the fact that electroporation might not be applicable to large animals and humans, and also given the lack of a complete effect, the suitability of the present invention for enabling DNA cellular entrance and expression was examined.

Part 2—Laser Interaction Study

Figure 4:
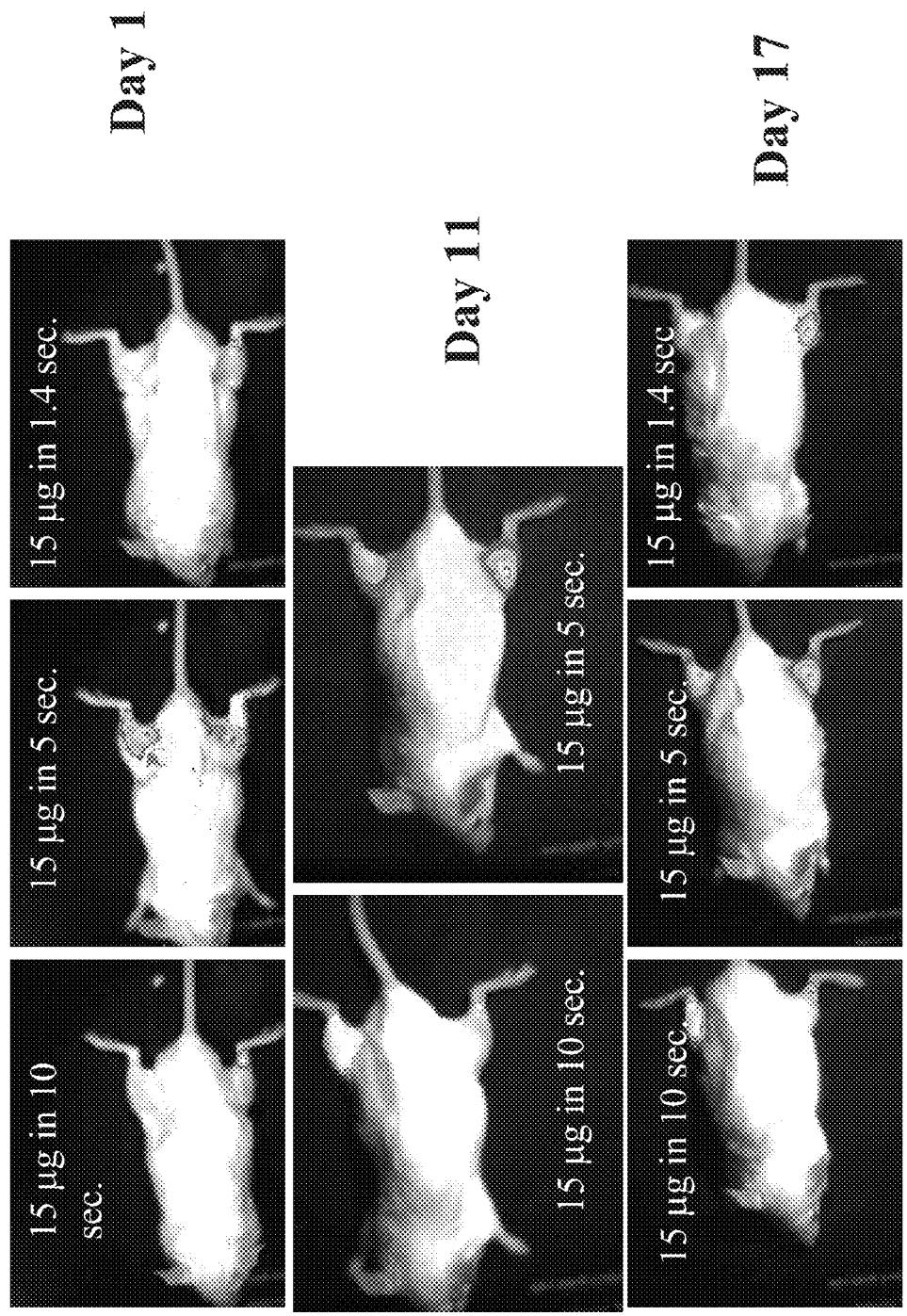
FIG. 4. Time kinetics of luc expression following laser beam application compared to electroporation. BALB/c mice were injected with 15 μg pLNC/Luc in the muscle of both dorsal legs of the mice. This was followed by electroporation in the right back leg or treatment with a laser beam in the left back leg. Luc expression was followed from day 1 to day 30. Three groups of mice were assessed based on the length of time that the laser beam was applied. The laser beam was applied for 1.4, 5 and 10 seconds in each one of the groups.

The effect of an external laser beam was assessed for its potential to support DNA transduction in muscle cells after naked DNA injection. Side by side in the same animal, laser beam transduction was compared to DNA electroporation into muscle cells. BALB/c animals were used in this experiment; as for Part 1 above, these experiments were conducted with mice in groups of three mice, and were performed between two to three times repeatedly. The luc expression cassette and detection system was also applied as described in Part 1 above; the results are shown in FIG. 4. FIG. 4 shows time kinetics of luc expression following laser beam application compared to electroporation. Luc expression was followed from day 1 to day 30, although FIG. 4 only shows results at days 1, 11 and 17. The laser beam was applied for 1.4, 5 and 10 seconds to mice in each one of three groups of mice. Comparison of the electroporation method to the laser beam application after one day revealed that the level of expression following the 10 second laser beam application is in the same range of the electroporation transduction. Laser beam application of 15 seconds did not induce sufficient luc expression.

Figure 5A:
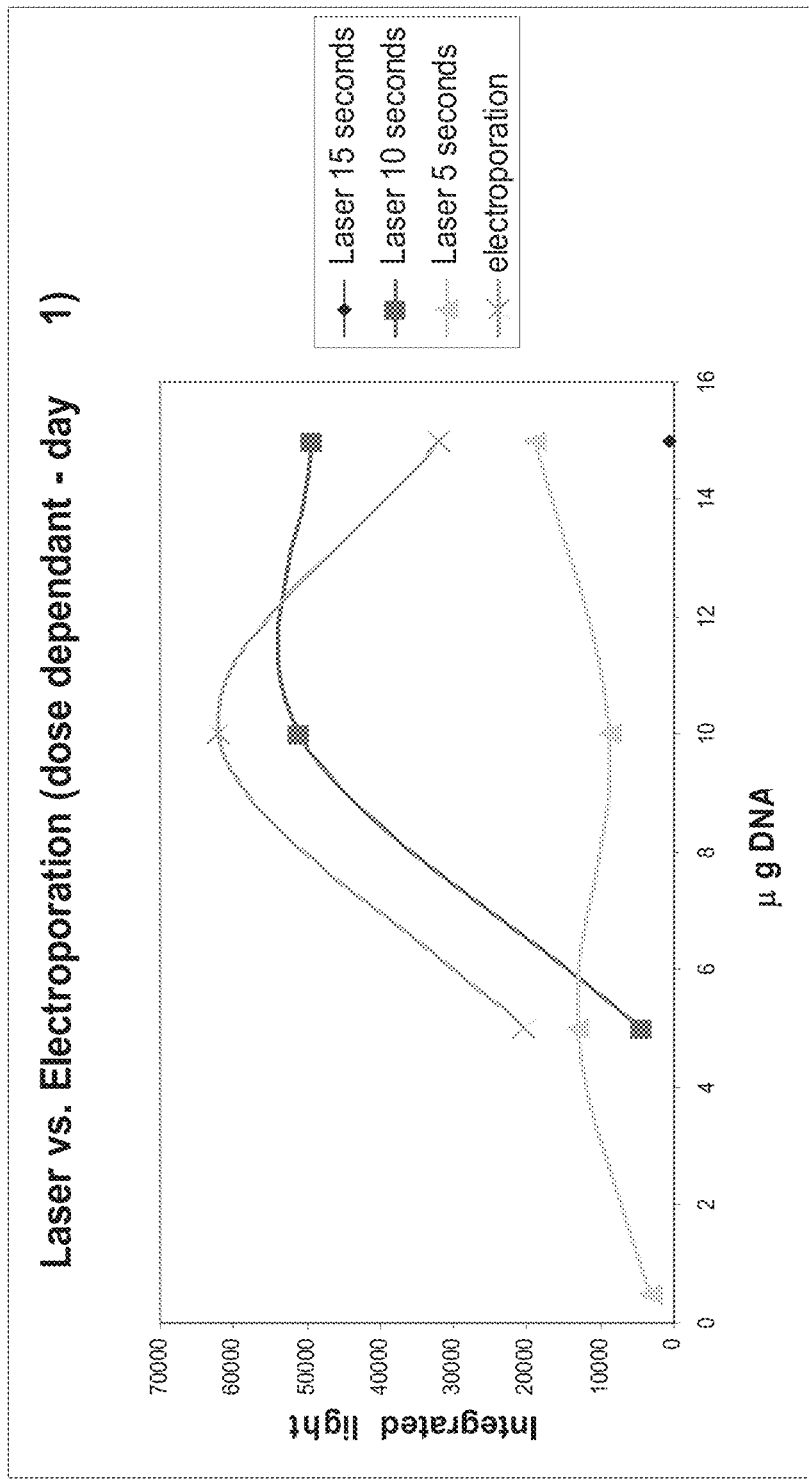
FIG. 5. A dose response analysis of laser beam duration compared to electroporation (A). BALB/c mice were injected with 15 μg pLNC/Luc in the muscle of the dorsal legs of the mice. This was followed by electroporation or treatment with a laser beam. Luc expression was assessed on day one. Three groups of mice were assessed based on the length of time that the laser beam was applied. The laser beam was applied for 5, 10 or 15 seconds in each one of the groups. This was compared to the electroporated treated group over time (B).
Figure 5B:
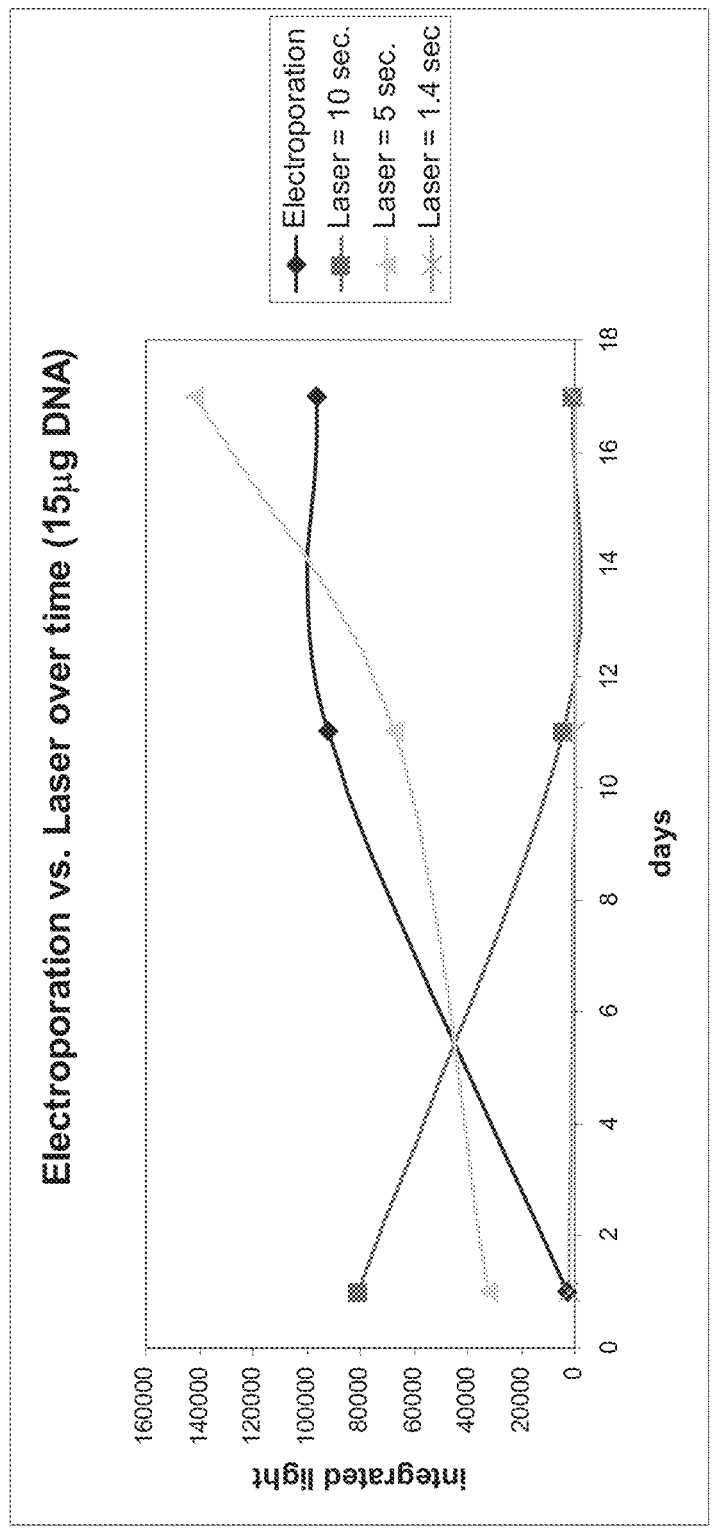

For the assessment of laser beam gene transduction, luc expression was determined by using the same animal model, comparing again electroporation to the laser beam application. FIG. 5 shows a dose response analysis of laser beam duration compared to electroporation. Luc expression was assessed on day one (FIG. 5A), or from 1-18 days (FIG. 5B). The laser beam was again applied for 5, 10 or 15 seconds in each one of the groups. This was compared to the electroporated treated group. As shown in FIG. 5, laser beam application of 5 seconds had a similar and even a significant higher transduction effect than the electroporation approach, both on day one but even more strongly on the results obtained 17 days after administration.

Part 3—Additional Studies of Laser Treatment for Gene Therapy

As described in greater detail below, the potential clinical application of the laser treatment of the present invention was assessed, by using it to transfer the murine erythropoietin (mEPO) gene into mice. Laser treatment-mediated mEPO gene delivery resulted in elevated (>22%) hematocrit levels that were sustained for 8 weeks. Gene expression following laser treatment was detected for >100 days. Hence, the laser treatment of the present invention is a simple, safe, effective and reproducible method for therapeutic gene delivery with significant clinical potential.

These studies also enable system testing to be performed, which revealed that injection of 10 μg naked DNA to the tibial muscle of mice followed by application of the laser beam for 5 sec, focused to 2 mm depth upon an area of 95 micro-m$^2$, resulted in the highest intensity and duration of gene expression with no histological or biochemical evidence of muscle damage, for this particular example.

The results of these additional studies are described in greater detail in the sections below.

Gene Expression and Dose Response Experiments Following Femtosecond Laser Beam Application As described above, the model system used a femtosecond infrared mode-locked Ti:Sapphire laser as an illumination source (see Materials and Methods). The energy source was an argon ion laser and the beam was focused onto the tissue by an inverted microscope. Laser beam interaction with the tissue depends on current intensity, pulse number, pulse duration, surface laser beam area, and the depth of focus. For this example, the duration of the laser beam pulse was from about 1 to about 25 sec, the focus was for depths of from about 0.1 to about 15 mm, and the laser beam area was about 95 mm$^2$. It should be noted that these are intended as illustrative examples only.

To optimize these parameters for these conditions, the tibial muscles of mice were injected with a DNA plasmid (pLNC/Luc) encoding the firefly luciferase gene. The plasmid DNA (1 micro-g to 15 micro-g dissolved in 0.9% saline) was administered by injection in a volume of 30 micro-l followed 30 seconds later with either electroporation (EP) on the right leg (16 consecutive 20 millisecond square-wave pulses at a field strength of 200 volts/centimeter), or by application of an ultrashort pulsed laser beam (LBGT) on the left leg.

Figure 6A:
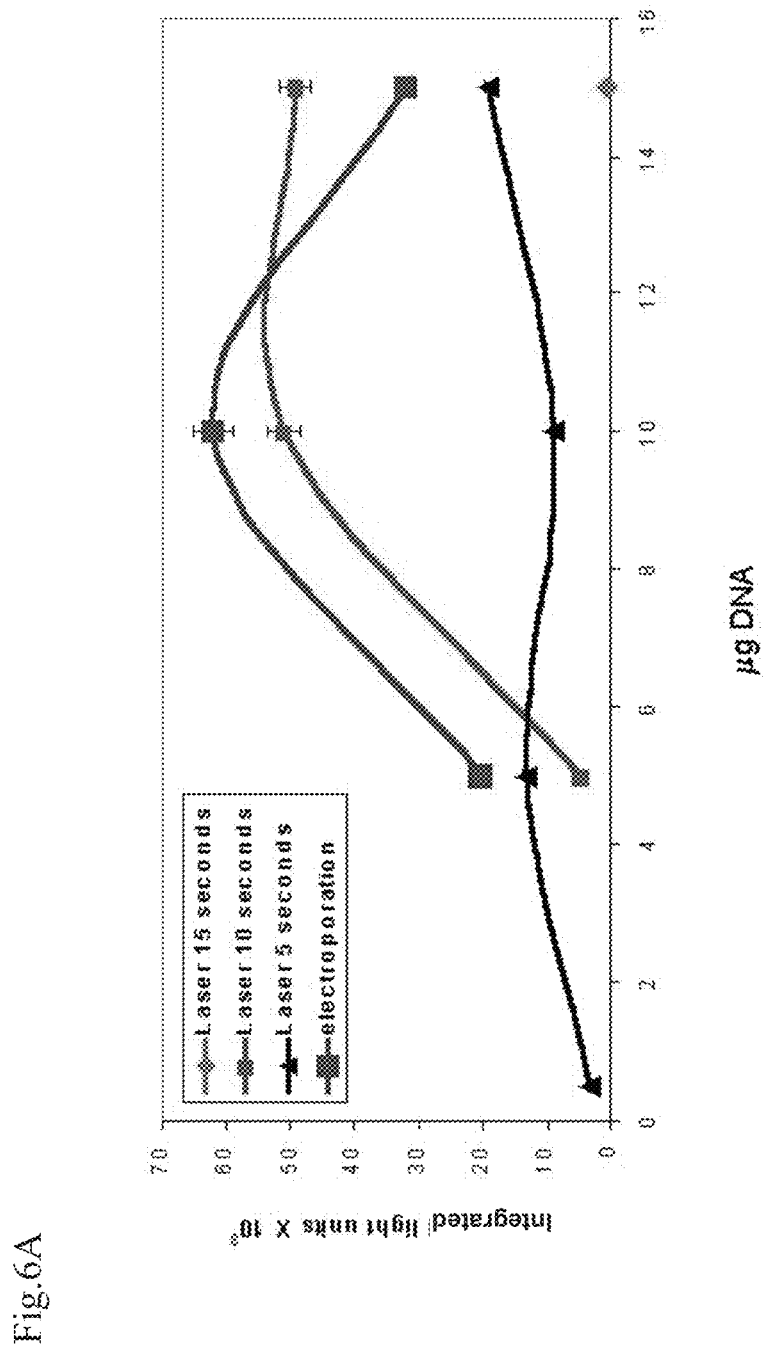
FIG. 6. Comparison of Laser (LBGT) to Electroporation (EP) gene delivery. (A) For a dose response experiment assessing gene expression on day one, BALB/c mice were injected with 0.5-15 micro-g pLNC/luc DNA. Thirty seconds later the legs were either electroporated (right leg) or exposed to a laser beam (left leg). The laser beam was applied at a surface of 95 im$^2$, at a depth of 2 mm, for 5, 10 or 15 seconds (in the 15 second laser beam exposure group no gene expression was seen. One representative point is depicted). The leg was exposed to the laser beam 10 times in a rotational manner around the site of injection. Real time in vivo continuous luc expression was monitored with a biochemiluminescence CCCD system. The pictures show mice injected i.m. into the right and left legs with (B) 10 micro-g and (C) 15 micro-g pLNC/luc DNA per leg for 5 seconds exposure for the LBGT side. As can be seen in parts D and E, despite the significant advantage to EP (D) on day 23, this advantage disappears over time and the laser (E) and electroporation methods give the similar results.

Pulse timing was also optimized for these conditions, by comparing durations of 5 to 15 seconds. Luciferase gene expression was followed by monitoring light emission using a bioluminescence cooled charged-coupled device (CCCD) detection system (see Honigman, A., Zeira, E., Ohana, P., Abramovitz, R., Tavor, E., Bar, I., Zilberman, Y., Rabinovsky, R., Gazit, D., Joseph, A., Panet, A., Shai, E., Palmon, A., Laster, M., and Galun, E. (2001). Imaging transgene expression in live animals. *Mol Ther* 4: 239-249, previously incorporated by reference). It was observed that injection of 10 micro-g DNA was optimal and resulted in similar levels of luciferase expression with both the EP and the LBGT methods (FIGS. 6a-6c). FIG. 6A shows that for a dose response experiment assessing gene expression on day one, BALB/c mice were injected with 0.5-15 micro-g pLNC/luc DNA. Thirty seconds later the legs were either electroporated (right leg) or exposed to a laser beam (left leg). The laser beam was applied at a surface of 95 im$^2$, at a depth of 2 mm, for 5, 10 or 15 seconds (in the 15 second laser beam exposure group no gene expression was seen. One representative point is depicted). The leg was exposed to the laser beam 10 times in a rotational manner around the site of injection. Real time in vivo continuous luc expression was monitored with a biochemiluminescence CCCD system. FIGS. 6B and 6C show mice injected i.m. into the right and left legs with (B) 10 micro-g and (C) 15 micro-g pLNC/luc DNA per leg for 5 seconds exposure for the LBGT side.

The optimal pulse duration was 10 seconds for gene expression after one day, however, subsequent experiments revealed a significant advantage of using a 5 second pulse for inducing longer expression (see following results).

Figure 6D:
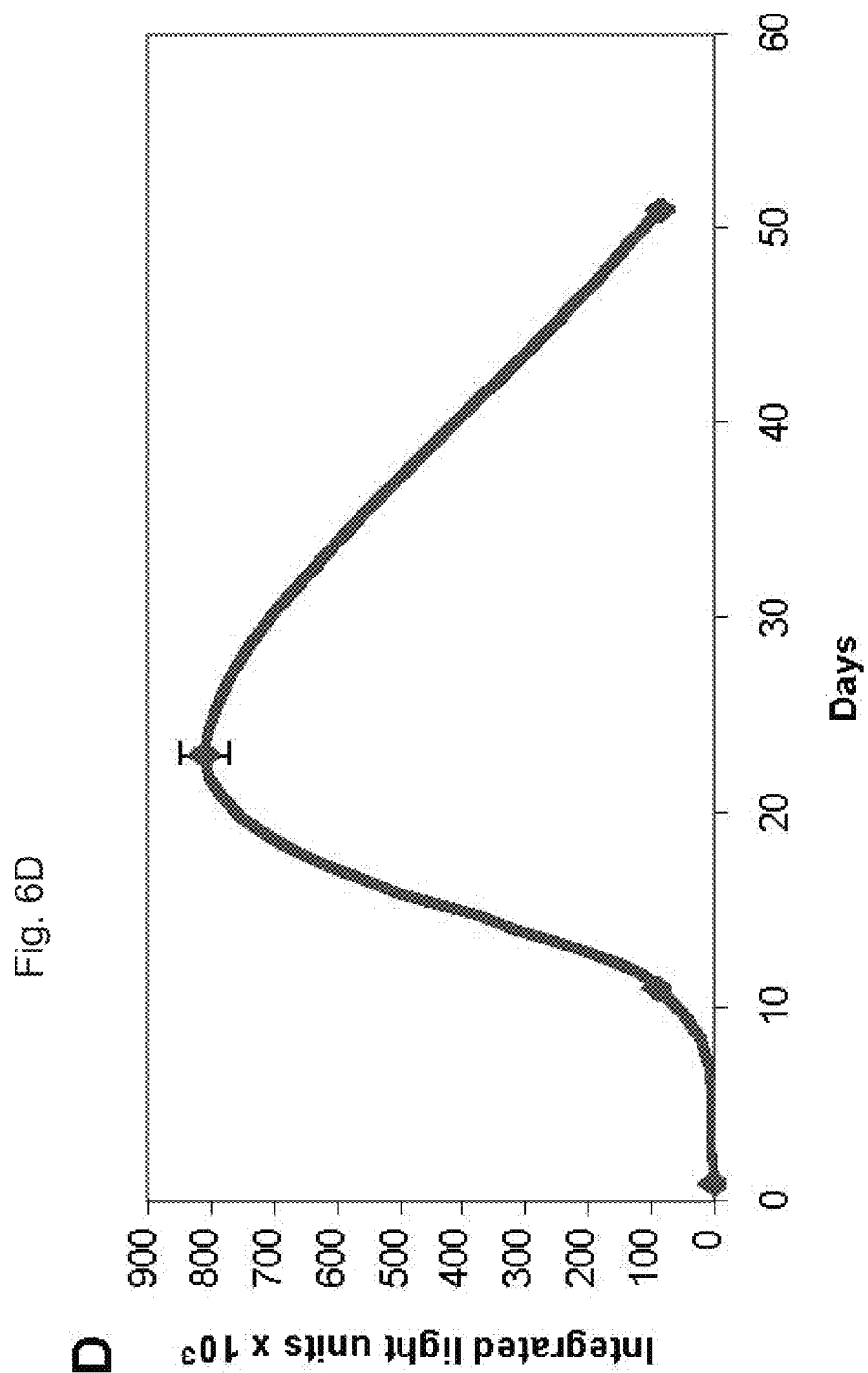

Intramuscular Gene Delivery Efficiency of the Femtosecond Laser vs. Electroporation Compared Over Time To comparatively assess the duration of the plasmid expression with LBGT and EP, the same naked DNA construct was injected into the tibial muscles of BALB/c mice followed 30 seconds later by electroporation, or by application of laser beam pulses (10 pulses rotationally, surface of 95 micro-m$^2$, focus of 2 mm, pulses duration of 5 seconds, current intensity of 30 mwatt). Luciferase expression was monitored for over 60 days (FIGS. 6d and e). While gene expression mediated by EP was higher on day 23 (shown in FIG. 6d), the observed differences between EP and LBGT disappeared over time and on day 52, expression levels were similar for both treatment methods (see FIG. 6e for the results with laser treatment).

Testing of Laser Beam Parameters

Figure 7A:
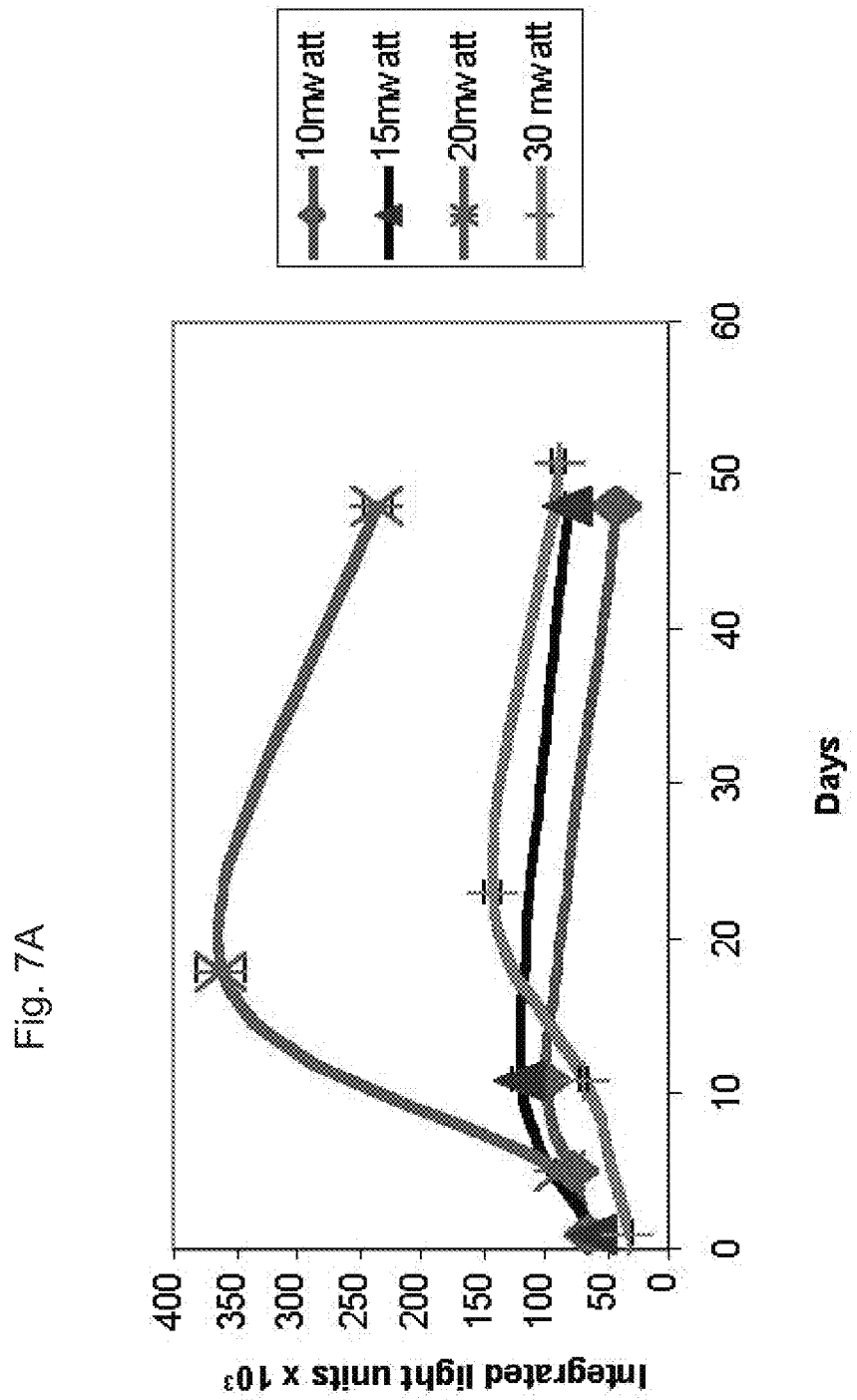
FIG. 7. Determination of optimal intensity, timing, focus and surface parameters. Mice were injected with 10 μg pLNC/luc DNA. Thirty seconds later the left leg was exposed to a laser beam 10 times in a rotational manner around the site of injection. The efficiency of each parameter was checked over time. Intensity (A): Using 10-30 mwatts. Timing (B): The exposure lasted for 3-10 seconds. Presented are the integrated light units emitted at the site of injection above background. (C and D). For controls, 10 μg of pLNC/Luc was injected (left leg) followed by application of laser-beam and pLNC/Luc (right leg) without any pulses.
Figure 7B:
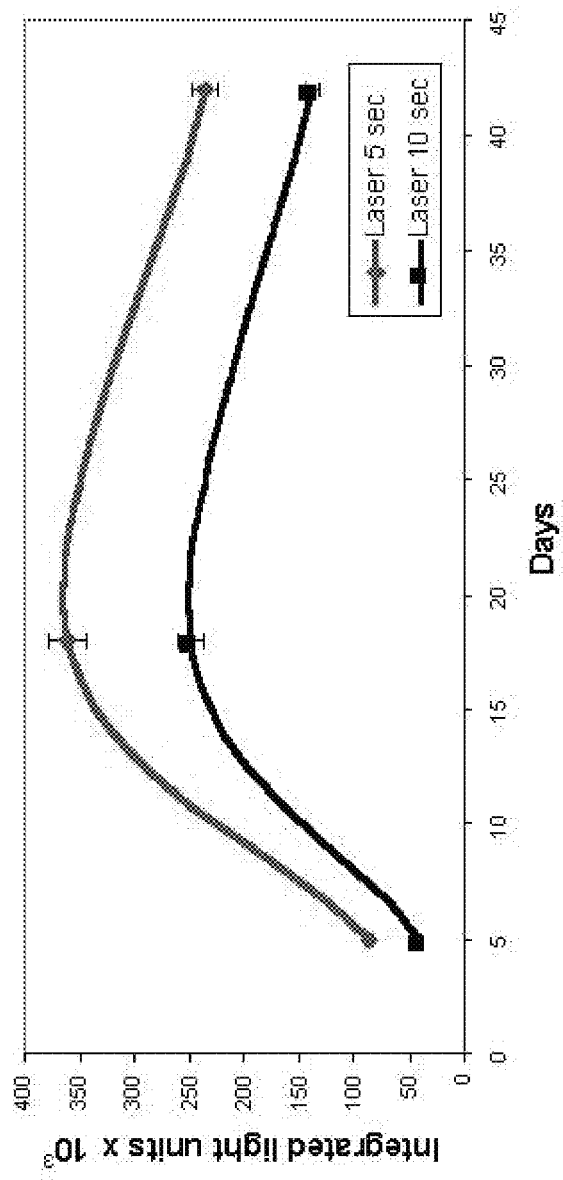

The laser treatment according to the present invention was further examined with regard to laser current strength (10 mwatt-30 mwatt) to determine its effect on gene expression. Luciferase expression increased by up to 3-fold at an intensity of 20 mwatt, but declined thereafter (FIG. 7a). Using the optimized conditions for these experimental conditions (20 mwatt current strength, surface area of 95 micro-M$^2$ and depth of 2 mm), pulse duration was varied between 3-10 seconds, to examine the relationship between these parameters. The highest luciferase expression levels (integrated light units) were achieved with pulses of 5 seconds as shown in FIG. 7b. Expression efficiency was examined as an outcome of varying the muscle surface area exposed to the laser beam. Surface areas ranging from 40 micro-m$^2$ to 120 micro-m$^2$ were evaluated, and the optimal surface for these experimental conditions was determined to be 95 micro-m$^2$ at a current intensity of 20 mwatt with a 5-second pulse (data not shown). In the same experiment laser beam depth of focus into the muscle was also optimized for these experimental conditions, varying it from 1 to 3 mm, adjusted to the depth of the muscle tissue, and observed that 2 mm was optimal for these conditions (data not shown).

It is likely that the application of LBGT to other animal species will require similar optimization steps, such that preferably the conditions for laser treatment according to the present invention are optimized according to the method described herein for human treatment or for treatment of lower mammals. Similar processes as described above could optionally and preferably be performed for different species, and/or treatments and/or tissues being treated.

Figure 7C:
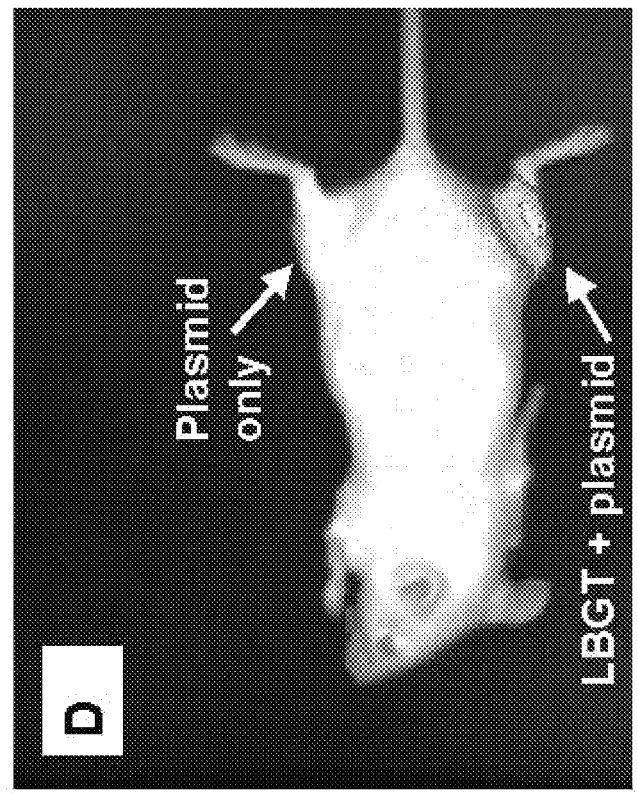
Figure 7D:
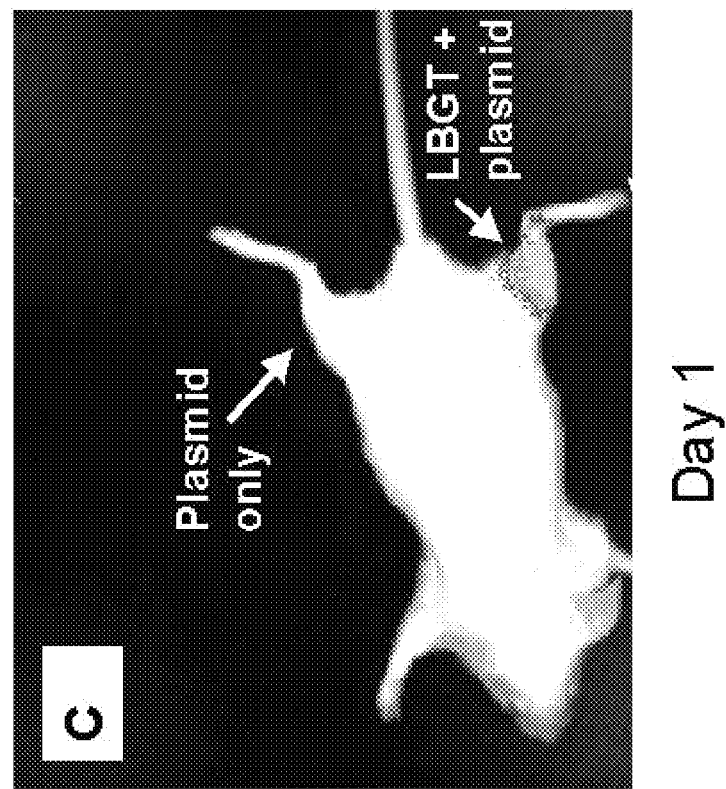

In all subsequent experiments in mice LBGT the optimized conditions used were: laser beam intensity of 20 mwatt; surface area of 95 micro-$M^2$; pulse duration of 5 seconds; and focus of 2 mm. LBGT-assisted gene delivery was compared to naked DNA administration without assistance, in mice. Both left and right tibial muscles were injected with the luciferase pLNC/Luc vector, but only the left leg underwent LBGT (using the conditions described above). FIGS. 7c and 7d show two controls, for which 10 μg of pLNC/Luc was injected (left leg) followed by application of laser-beam and pLNC/Luc (right leg) without any pulses. FIGS. 7c and 7d demonstrate that on both day 1 and day 48, light was emitted only from the laser treated left leg. These results were reproducible and consistent in replicate experiments (data not shown).

Localization and Comparative Evaluation of Gene Expression After EP and LBGT

Figure 8A:
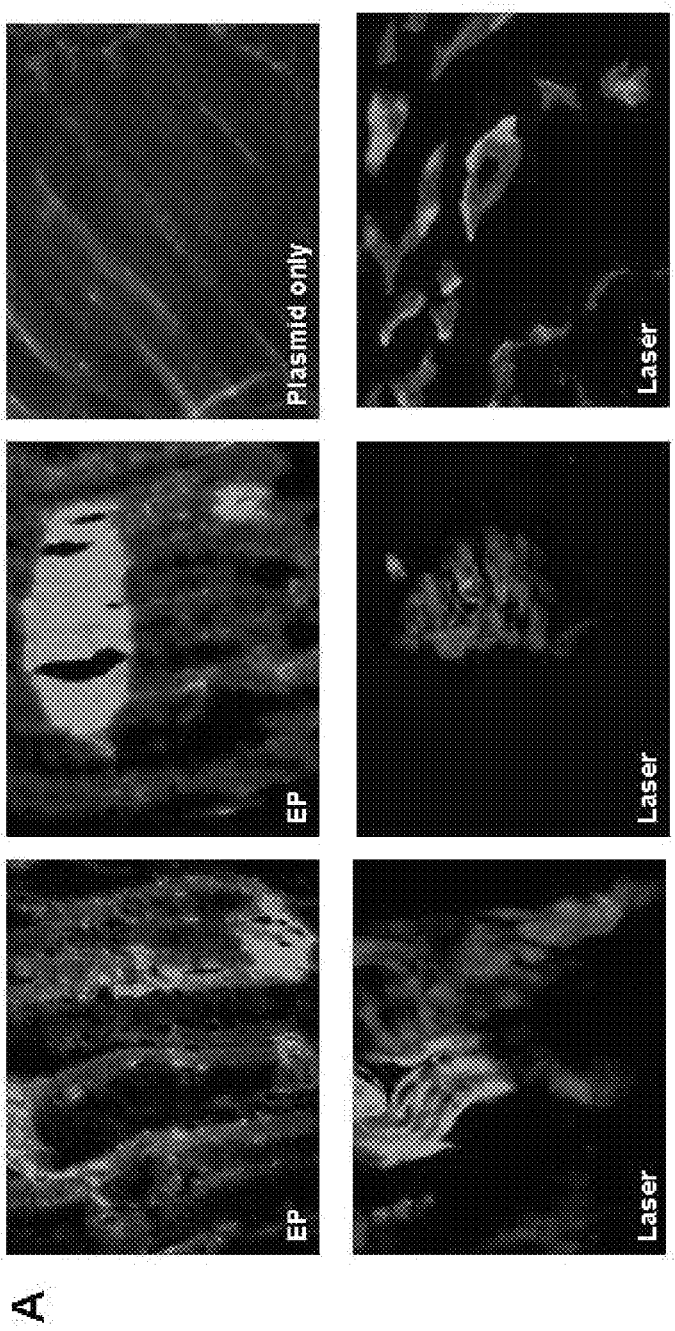
FIG. 8. Reporter gene assessment—an immunohistochemical study: (A) Muscle GFP gene expression: For GFP gene expression, the muscles were frozen in OCT tissue embedding medium and sectioned (6 μm) under cryostat. Sections were placed on polylysine-coated slides, fixed in acetone for 30 sec and GFP expression was observed directly by fluorescence microscopy. (B) Muscle Luciferase gene expression: Paraffin-embedded sections were pretreated by incubation in citrate buffer and heated. After incubation at room temperature with rabbit polyclonal antibodies against luciferase, sections were then washed and incubated with biotin-conjugated goat antibody anti rabbit. After this treatment, the samples were labeled with peroxidase conjugated streptavidin and detected using 3-amino-9-ethyl carbazole substrate (see materials and methods). (C) Muscle gene β-gal expression: The electroporated, laser-beam-application and muscle-injected-with-plasmid-only tissues, were excised and analyzed for the presence of β-gal six days post DNA injection (see materials and methods). The whole-mount X-gal stained tissues were then photographed. The tissues were then paraffin embedded and sections were fixed, washed in PBS containing 2 mM MgCl$_2$, and stained. Image analysis was performed using a light microscope (40× magnification). As can be seen with the GFP, β-gal and luciferase reporter genes, both the EP and LBGT methods resulted in similar expression. Plasmid-injected-only sections show extremely weak expression. The arrows indicate single cell plasmid expression, which can be seen in both luciferase and β-gal.

The tissue distribution and localization of reporter genes was assessed following injection with naked DNA alone, or with EP, or with LBGT (laser). the reporter genes used were one of green fluorescence protein (GFP, FIG. 8a), luciferase (FIG. 8b) or β-galactosidase (FIG. 8c). Plasmids were injected into the muscle without any pulsed assistance, or with EP or LBGT. Six days later mice were sacrificed, the injected muscles were excised, and reporter gene expression levels were determined semi-quantitatively by direct fluorescence or immunostaining.

Figure 8B:
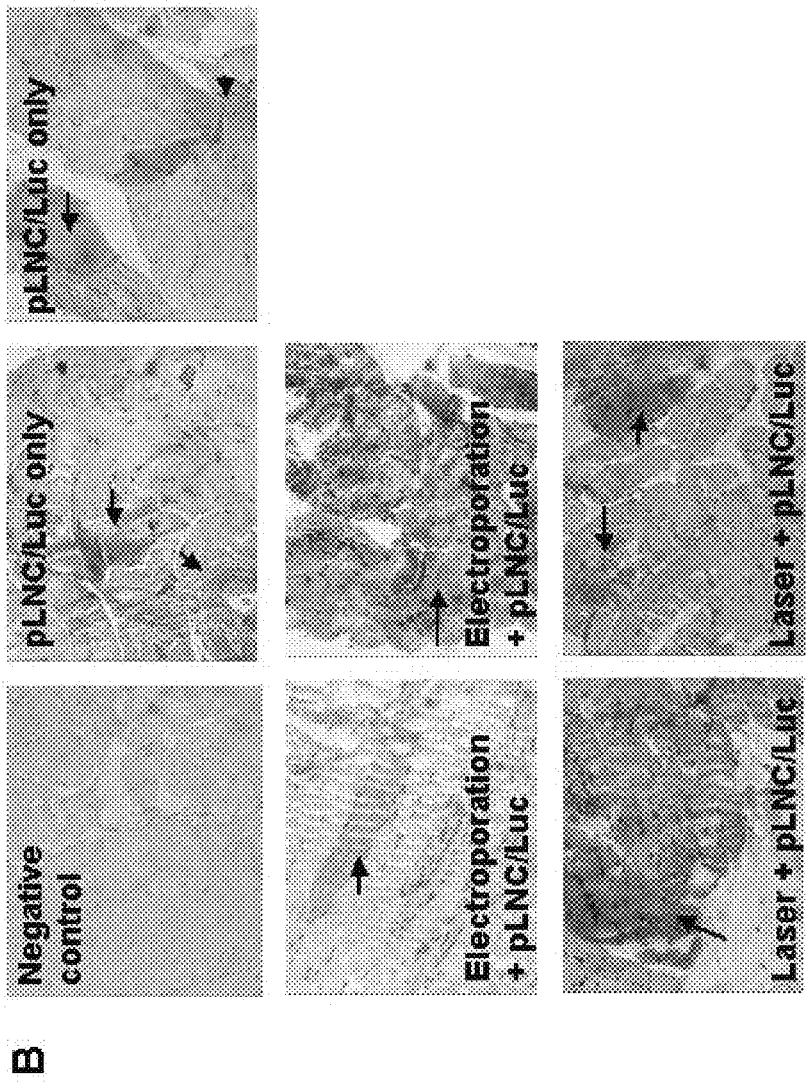

FIG. 8A shows two different electroporation (EP) examples for muscle injected with GFP as the reporter gene, one plasmid only (injection of naked DNA only without further treatment) example and three different laser examples. FIG. 8B shows one negative control (e.g. no action taken), two positive controls (injection of naked DNA only without further treatment), two examples of treatment with EP and injection of naked DNA, and two examples of treatment with laser and injection of naked DNA, all with luciferase as the reporter gene, again using muscle samples. FIG. 8C shows three examples of treatment with EP, two positive controls (injection of naked DNA only without further treatment), and three examples of treatment with laser and injection of naked DNA, all with β-galactosidase as the reporter gene, again using muscle samples. It should be noted that the above description is provided according to the order in which the photographs appear within each figure.

In the group receiving the naked DNA plasmid expression cassettes without EP or LBGT, very little gene expression was detected (FIGS. 8a, b, and c). In contrast, when the plasmids were injected into the muscle, and followed with either EP or LBGT, groups of muscle cells expressed the reporter genes (FIGS. 8a, b and c).

Muscle Histological and Biochemical Changes Related to pLNC/Luc Gene Delivery

Figure 9B:
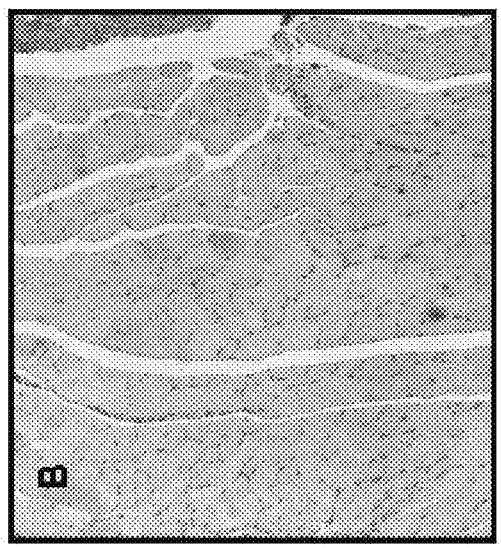
FIG. 9. Histology. Extensive and irreversible damage of skeletal muscle after electrical trauma can be ascribed to secondary release of myoglobin and CPK because of increased skeletal muscle cell membrane permeabilization. No tissue alteration was detected 24 hours after LBGT, and 48 hours post injection (A), the presence of areas with rare fibers with central nuclei was the only change in the laser beam stimulated muscles. These areas are considered as an unspecific sign of disturbance of muscle function. The damage was transient, and 70 days after treatment muscles appeared normal (B).
Figure 9A:
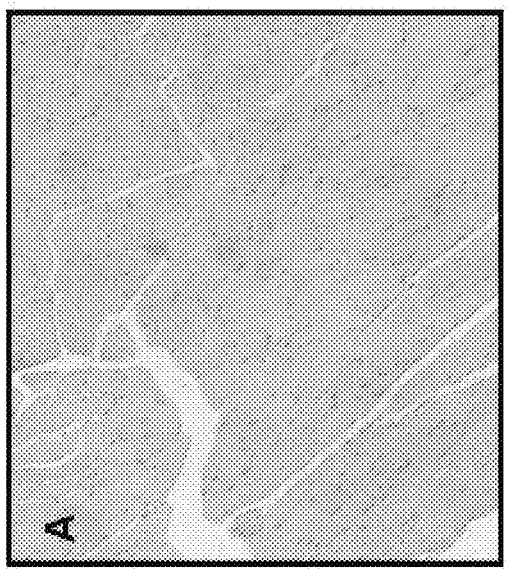

EP is known to induce muscle tissue injury (6, 13) evidenced histologically by necrosis with intense interstitial edema, inflammatory cell infiltration, myophagy, in addition to other signs of muscle degeneration and regeneration (13, 14). To evaluate the impact of LBGT on muscle tissue of mice, 10 micro-g of plasmid pLNC/Luc was injected into the tibia muscle followed 30 seconds later with a pulse from the femtosecond laser using the optimal conditions described above. Twenty-four, 48 hours and 70 days later, the mice were sacrificed and the muscle tissues were examined histologically. No tissue alterations were seen 24 hours after LBGT. At 48 hours, rare fibers with central nuclei was the only change observed in the LBGT group, suggesting mild tissue disturbance. This appeared to be transient and was not observed at 70 days after LBGT when the muscle tissue appeared normal. FIG. 9a shows muscle tissue after 48 hours; FIG. 9b shows muscle tissue after 70 days.

Naked DNA administration to muscle may, in itself, cause direct muscle injury. To further assess the level of muscle damage following naked DNA administration, EP or LBGT (laser), creatine phosphokinase (CPK) levels were determined in the serum of mice two hours after DNA administration. FIG. 10 shows that the level of CPK activity levels in mice treated with LBGT was six fold lower compared to those treated with EP. Surprisingly, CPK levels observed in the LBGT group were lower than in mice receiving only naked DNA. This observation was reproducible in a subsequent experiment (data not shown).

Erythropoietin Expression After LBGT-Assisted Delivery of Naked DNA Carrying the mEPO Gene.

Figure 11:
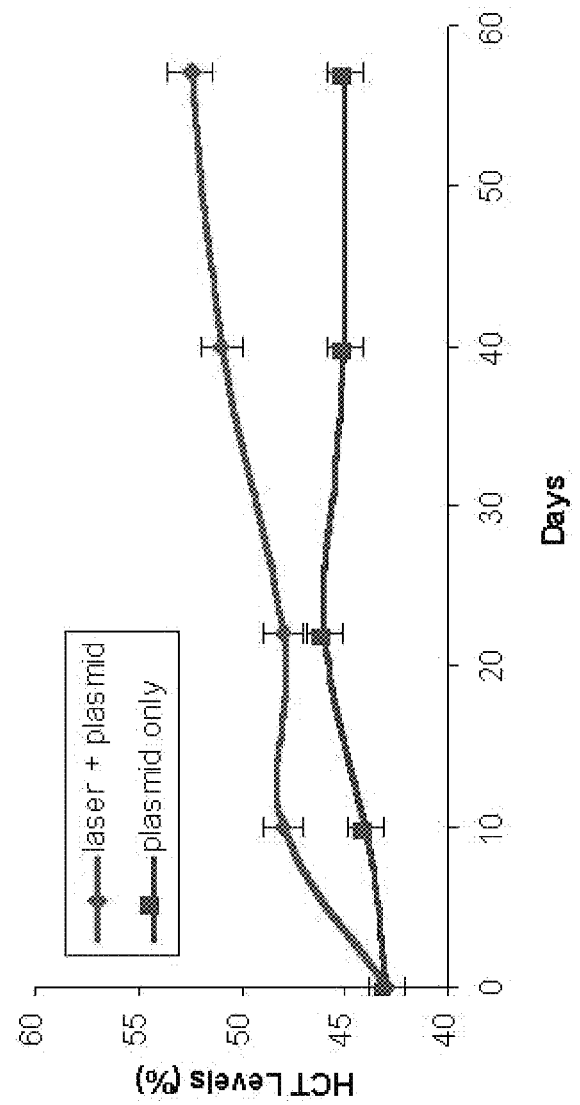
FIG. 11. To examine the therapeutic potential of the laser beam method, a plasmid encoding mouse erythropoietin (pcDNA.3mepo) was used. The pcDNA.3mepo plasmid was injected intramuscularly with 10 μg of either the pcDNA.3mepo plasmid, or the backbone pcDNA.3 (negative control) and followed by laser application. Blood was collected at various time points, and levels of Hct were determined.

To test the therapeutic potential of LBGT method of gene delivery, a plasmid (pcDNA.3mepo) encoding the mouse erythropoietin (mEPO) gene was used. In a dose response experiment, the plasmid was injected into the tibial muscle in a volume of 30 micro-1. The most effective dose was found to be 10 micro-g (data not shown). Mice were injected intramuscularly with 10 micro-g of either the pcDNA.3mepo plasmid, or the backbone plasmid, pcDNA.3 (negative control) with or without LBGT. Blood was collected from the orbital plexus at various intervals after treatment, and hematocrit (Hct) levels were determined. In mice that received pcDNA.3mepo without LBGT, Hct levels were not different from those of negative control mice (data not shown). In the group who received pcDNA.3mepo with LBGT, Hct levels were higher than the levels of those receiving the negative control plasmid with LBGT, throughout the period of evaluation, and were significantly (p=0.05) higher at 22% at 8 weeks (FIG. 11).

These experiments indicate that the laser beam gene transduction method could be use for inducing gene expression after naked DNA administration into the muscle and probably to other organs.

Discussion

Gene therapy is currently at a critical turning point (15) from the "proof of principle era," in which some viral based protocols and therapeutic platforms had shown some promise (16), into a period where safety issues of the delivery have emerged as prominent factors in the choice of therapeutic modalities. A recent report (http://www.esgt.org/; and http://www.asgt.org/) concerning the development of a lymphoproliferative disorder in a child treated for X-SCID with an integrating retroviral vector spotlighted vector safety issues. These risks occur when the viral and non-viral-integrating (such as the use of transposable elements) gene delivery methods are utilized (17). While various novel tools have recently been developed for site-specific correction of point mutations (18) no level of risk is considered clinically acceptable. Non-viral gene delivery approaches while encouraging in some experimental situations, have generally been relatively unsatisfactory for clinical applications. Various ways of overcoming the problems associated with non-viral gene delivery have been explored including: linking viral proteins to DNA to enhance penetration of cell membranes (19); and novel techniques which enhance the transport of DNA from the cytosol to the nucleus such as the use of nuclear targeted receptors like the, glucocorticoid receptor (20). Another approach that has met with some success experimentally in small animal models, is intra-arterial injection of naked DNA (plasmids expressing the gene of interest) into limb muscle (21). Intrauterine injection of DNA with microbubble-enhanced ultrasound (22) has also been used experimentally in fetal gene therapy. However, all of these systems fall short of their targets, as they are too complicated for clinical use.

Currently, the most promising non-viral gene delivery approach for high protein expression is electroporation (EP) of muscle into which naked DNA has been injected. In general, two types of approaches have been tried: high voltage/short pulse; or low voltage/long pulse. So far, the highest plasma levels of an encoded protein after muscle EP have been obtained with repeated low voltage (~200 V/cm) at long pulses (20 ms) (23). A recent report (24), compared adverse outcomes and tissue toxicity of the EP and adenoviral gene transfer methods. Following muscle EP, histological examination revealed muscle necrosis with severe polynuclear and mast cell infiltration, which was maximal at day 7 after treatment. Histological changes were accompanied by elevation in CPK between day 7 and 14, suggesting the possible development rhabdomyolysis, which in humans could lead to kidney failure. The degree of muscle damage and necrosis was correlated with the voltage intensity. Unfortunately, at lower transducing voltages of 50-100 V/cm gene expression was found to be very low. Furthermore, the degree of muscle injury was comparable to that observed after adenovirus-mediated gene administration to the muscle. Hence, better gene delivery methods are needed to enhance DNA delivery into muscle tissue as well to other organs. The present invention provides a simple, more effective and safe gene delivery method which uses laser pulsed gene transduction.

In this study, successful expression of a foreign gene in the tibial muscle of mice was demonstrated, following a femtosecond laser beam application after injection of naked DNA. This expression is higher than that observed with naked DNA administration per se and comparable to that observed when naked DNA administration combined with EP. The application of the laser beam to the muscle tissue of the mice proved to be gentle and could be specifically focused to a small area of a muscle injected with a low amount of DNA and in a small volume. Moreover, it should be possible to apply this technique of gene transduction to larger surface areas of muscle tissue with larger volumes and higher amounts of DNA. This would simplify targeting of the laser beam to the desired area, allowing this method to be used for gene delivery in larger animals or humans. As the laser was not found to be damaging to muscle tissue, this technique should allow scanning of a larger skin area of the skin to maximize the number of muscle fibers that are transfected. Additional technologies could also be combined with laser beam gene transfer to enhance DNA accessibility to the muscle such as the use of hyaluronidase and other DNA uptake-enhancing components that could be mixed with the DNA solution.

An alternative and easier target for this laser beam technology is the skin, itself. Recent reports have suggested various methods to enhance gene expression in the skin. Some use retroviral vectors (25) or other integrating technologies (14), and hence, impose safety considerations. EP protocols were also used for skin gene transfer for vaccination. Some tissue damage was apparent with even relatively low energy pulses (26). Hence, naked DNA injection into the cutaneous tissue followed by the application of the femtosecond laser beam could also be useful for vaccination.

The novel method described in this report is based on the potential of the femtosecond beam to enhance the transfer of plasmid DNA across mammalian cell membrane as recently reported (27). The mechanism by which electric pulses or infrared laser beam application (femtosecond) induces DNA movement across cell membranes is not understood at this time. Electrophoretic forces or laser beam minimal heating effects caused by multiphoton disruption may cause DNA accumulation at the cell interface, facilitating DNA insertion though the membrane. The laser beam may also "porate" the cell membranes, enabling a transient transfer of DNA into the cellular cytosol and later, into the nuclear compartment. As shown herein, this method is effective, simple, and safe for use in muscle tissues of mice. The prolonged expression reporter genes in mice observed in this study is expected to be reproducible in studies with larger animals. The focus of the laser beam developed could be adjusted to between 0 to 10 mm below the skin level. This could enable expression of the transduced gene in either one of two tissues, skin or muscle, in humans. Future developments would probably also open the way for the application of this method to other organs and indications.

In conclusion, femtosecond lasers have great potential as a therapeutic delivery tool in medicine. Their application allows for tissue effects with minimal collateral damage where the effects of the light can be confined to a specific layer of tissue under the skin or for that matter on the skin surface. This can be accomplished at depths of several millimeters below the surface with indications in the experiments described herein that such effects of the fundamental beam can be as deep as a centimeter. These lasers also provide a good connection to diagnostic techniques such as optical coherence tomography, which allows for in situ cytological analysis of the effects of the laser. Thus, where cold laser approaches are called for, these results indicate that the femtosecond laser has premier capabilities and will have great potential in therapeutic protocols. The results of this study have shown that femtosecond laser based gene transduction may, indeed, be a breakthrough in the current hiatus of non-viral-mediated gene therapy.

The present invention has a number of clear technical advantages. For example, the present invention includes the characterization of the optics that is required to accomplish the specific tissue alterations previously described, while also allowing for a new modality in gene therapy. The ability to characterize the higher order laser tissue interaction also permits the definition of the critical parameters needed for using other terms in the higher order expression discussed above to allow for functional imaging without destruction.

Specifically, the second order term of the higher order expression can now be used to perform second harmonic generation without tissue alteration, based on the in vivo parameters that have been defined by the operation of the present invention with gene transfection. Second harmonic generation enables membrane potential to be determined. The in vivo application in cellular systems or in tissue systems has been difficult without an in vivo assay for accurately determining the conditions of laser irradiation for keeping the tissue or cellular system functionally viable. As a result of this invention, this technique can now be used for effective diagnosis of membrane potential changes as a diagnostic of a variety of cellular phenomena, and for defining the basis of specific cell separation protocols using membrane potential as the basis of the separation.

The background art has not taught the user of higher order laser tissue interaction and/or has not applied this technology with the characterization methodology that is a preferred embodiment of the present invention. Such a characterization methodology is critical to the application of such technologies; the lack of such characterization is the reason that no therapeutic application of these technologies is currently available.

Example 2

Characterization of the Laser Tissue Interaction for AMD Treatment

The present invention was also tested for the treatment of AMD. The present invention uses a ultrashort laser in which focusing can be used to increase the fluence of the laser in a non-linear fashion to cause multiphoton absorption in a very narrow range around the focal spot which is under the retina and in the RPE where the pigment containing droplets form. The optional but preferred example of such a laser is a femtosecond (for example, $10^{-15}$ sec) laser, as described herein.

The objective is to cause such multiphoton absorption only in the tissue containing the fluorescent droplets while leaving the surrounding tissue untouched by the effects of the laser beam. Lasers can provide extreme control of such non-linear optical, multiphoton processes for microscopic illumination [T. Wilson and C. J. R. Sheppard, Theory and Practice of Scanning Optical Microscopy (Academic Press, New York 1984]. With such multiphoton absorption the excited state of the molecule in created and various studies have shown that a rule of thumb for the life of molecule before photochemical destruction or photobleaching is approximately $10^{-5}$ excursions through a molecular singlet state which is most probably the excited of the autofluorescent pigments excited in the RPE. Such singlet states last for approximately $10^{-9}$ secs and depending on the fluence the time for photochemical destruction of the molecule is effectively controlled.

In terms of ophthalmology this is similar to destroying the membrane that forms behind the lens in approximately 30% of the cataract removal procedures that are performed. In the case of cataract, the laser that is used to destroy this membrane is a nanosecond ($10^{-9}$ sec) neodymium yittrium aluminum garnet laser and the region in the focus of the beam where the fluence is sufficient to destroy the membrane is much larger than what can be achieved with present state of the art ultrafast lasers. In addition, in the case of nanosecond lasers the multiphoton effect that is employed is dielectric breakdown and associated mechanical destruction of the membrane and not multiphoton excited state absorption, which is a much gentler, photochemical, process.

Photochemical bleaching of the pigments related to AMD could delay the destructive effects of AMD. Even an alteration of a few years in the progress of the disease could have a significant effect on the onset of blindness in these patients who are significantly older than the average population.

Materials and Methods
Biological Preparations
In-Vitro Investigation

A series of in-vitro investigations were performed with post mortem fresh bovine and sheep eyes, which were obtained from a local slaughterhouse. The anterior segments of the eyes were removed. The eyes were prepared as an eyecup preparation: the vitreous was removed and the eyecup was filled with physiological media. A standard eye irrigation solution was used as the physiological medium. Fluorescein solution (30-50 µl, 10 mg/ml) and the synthetic AMD pigment, A2-E, solution, prepared by reported procedures [R. X.-F. Ren, N. Sakai and K. Nakanishi, J. Am. Chem. Soc. 119, 3619 (1997)], (30 µl, 0.16 mg/ml) was injected behind the pigment epithelium and the Bruks membrane of the eyes.

In-Vivo Investigation

All investigations involving animals were conformed to the ARVO resolutions on the *Use of Animals in Research*. White rats were used in these experiments. During the experiments, the animals were anaesthetized by injecting imalgene 1000 (ketamine) (Rhone Merieux, 0.1 ml per 100 g of animal's weight, 100 mg/ml). For opening the diaphragm of the animal's eye during the procedure, one drop of mydramide (Fisher, sterile eye drops) and one drop of Efrin-10 (Fisher, sterile ophthalmic solution) was added to the animal's eye. Also, a contact lens was placed on an animal's eye in order to allow for viewing the retina. A drop of methylcellulose 2% (oily eye drops) was put between the animal's cornea and the contact lens in order to improve contact between the lens and the cornea and to prevent drying and possible damage to the anterior tissues of an eye.

Fluorescein solution (10 µl, 10 mg/ml) was injected behind the pigment epithelium and the Bruks membrane of the eyes. After the treatment the animals were sacrificed and the eyes were taken for pathological examination in the Pathology Division of the Ophthalmology Department in the Hadassah Hospital. The eyes were fixed in 4% buffered formaldehyde for at least 48 hours. The tissue was embedded in paraffin and processed. Sections of 5-6 micron thickness were produced and were stained with hematoxylin-eosin.

Ultra Fast Laser System

Figure 12:
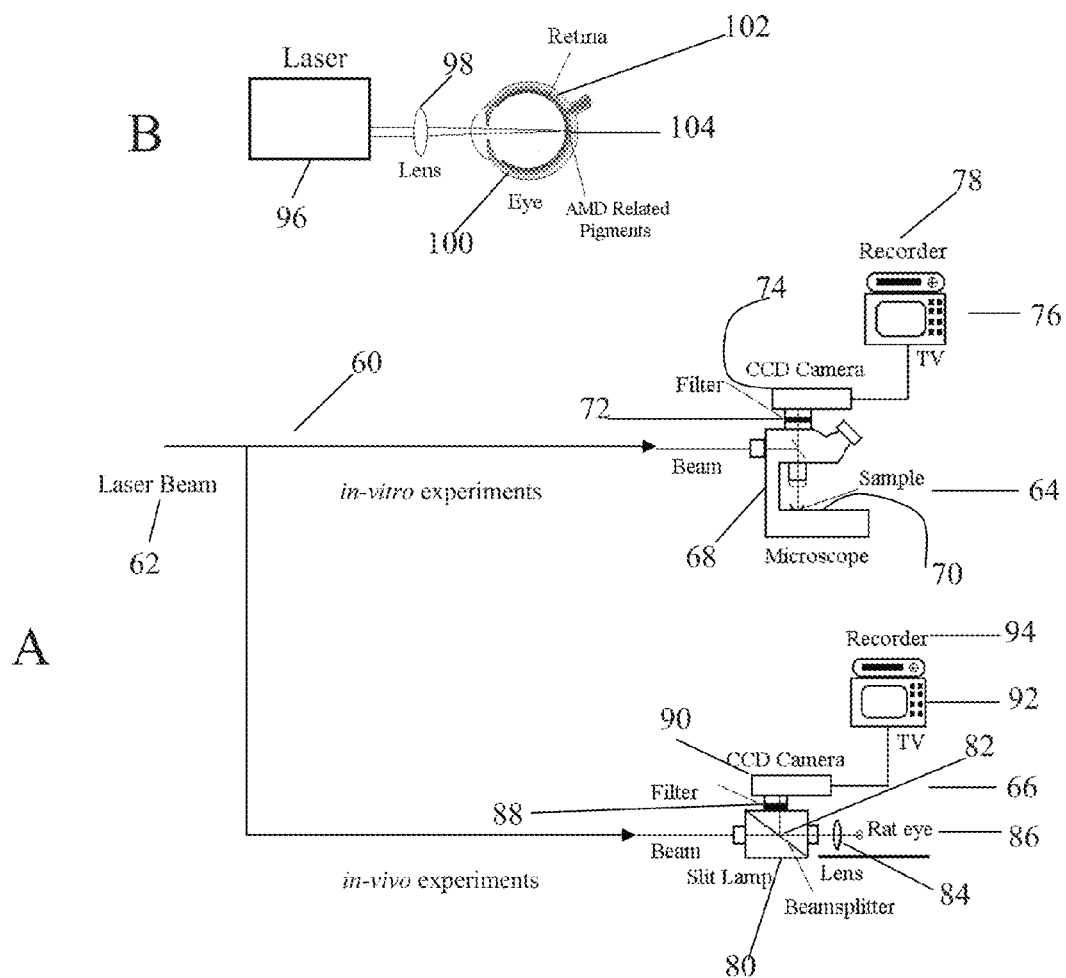
FIG. 12. Diagrammatic representations of the treatment of pigments in the in vitro and in vivo preparations and of the experimental laser system and associated devices used for these experiments.

As shown in FIG. 12A, another embodiment of a system 60 features both an in vitro 64 and an in vivo component 66. An ultrashort laser beam 62, or beam from an ultrashort laser, was produced by an ultrafast infrared mode-locked Ti:Sapphire laser (Coherent, Mira 900), as a non-limiting example of an ultrashort laser. It was pumped by an argon ion laser (Coherent, Innova 200) that was operated at 12 W in a multi-line mode (not shown). The operating wavelength was 800 nm, the pulse frequency was 76 MHz, and the pulse duration was about 0.200 psec. Beam diameter was 0.7 mm.

For the in vitro research (shown as component 64), laser beam 62 was transmitted via an upright microscope (Zeiss, Axioskop) 68 and was focused by ×40 N.A. 0.75 objective (Zeiss) on a sample 70 as described above. A CCD camera 74 (in this example a Sony camera, model SSC-C374) was attached to microscope 68 in order to allow for monitoring the procedure on-line. A filter 72, in this example a green filter, was placed in front of CCD camera 74 in order to cut off the infrared illumination of beam 62 (from the Ti:Sapphire laser). CCD camera 74 was connected to a TV (television) system 76 with a video recorder 78 where the relevant eye tissues and the dynamics of the green fluorescent excitation of the fluorescein or synthetic drusen were observed and recorded.

For the in vivo research (shown as component 66), laser beam 62 was transmitted via a slit-lamp 80, in this example a standard slit-lamp widely used in ophthalmological diagnosis. The slit-lamp magnification used was 16, 25 and 40. Slit-lamp also featured a beamsplitter 82. The infrared beam was focused under the retina of a rat's eye 86 using the slit-lamp lens (not shown) and a contact lens 84. The process was monitored and recorded as mentioned above, using (for the purpose of this example) the same CCD camera with the green filter attached to the slit-lamp and connected to the recording system, shown herein as a filter 88, a CCD camera 90, a TV system 92 and a recorder 94. Electrophysiological measurements can optionally be performed at the same time in this arrangement.

FIG. 12B shows a diagrammatic representation of a few components of the system of FIG. 12A, with more details of the eye in the sample. As shown, a laser 96, optionally and preferably the ultrashort laser of FIG. 12A, such as a femtosecond laser for example, produces a beam that is focused by a lens 98 onto a retina 102 of an eye 100 in the sample. The beam then destroys or at least reduces AMD related pigments (shown as reference number 104) which interfere with the vision of the subject.

Results and Discussion
In-Vitro Investigation

The experiments were performed on six bovine and six sheep eyes using fluorescin as a fluorescent material injected under the retina. The Ti:Sapphire laser beam intensity was 25-30 mW in these initial experiments where the objective was simply to address the geometric issues and the general feasibility of the experiment. With A2-E two bovine and three sheep eyes were investigated. The results of photobleaching are shown in Table 1. The duration of the photobleaching varied from case to case with the minimum being a few seconds, and the maximum being close to 3 minutes. This variation may probably be caused by parameters such as local concentration of the fluorescent material, exact location of the illuminated point behind the retina, etc.

TABLE 1

| Number of case | Type of the eye | Duration of bleaching | Type of the fluorescent material |
| --- | --- | --- | --- |
| 1 | cow | 0 min 6 sec | fluorescein |
| 2 | cow | 0 min 10 sec | fluorescein |
| 3 | cow | 2 min 50 sec | fluorescein |
| 4 | cow | 2 min 56 sec | fluorescein |
| 5 | cow | 0 min 27 sec | fluorescein |
| 6 | cow | 0 min 36 sec | fluorescein |
| 7 | sheep | 2 min 47 sec | fluorescein |
| 8 | sheep | 2 min 12 sec | fluorescein |
| 9 | sheep | 0 min 22 sec | fluorescein |
| 10 | sheep | 0 min 23 sec | fluorescein |
| 11 | sheep | 0 min 49 sec | fluorescein |
| 12 | sheep | 0 min 28 sec | fluorescein |
| 13 | cow | 1 min 05 sec | A2E |
| 14 | cow | 0 min 33 sec | A2E |
| 15 | sheep | 0 min 07 sec | A2E |
| 16 | sheep | 0 min 04 sec | A2E |
| 17 | sheep | 0 min 04 sec | A2E |

In-Vivo Investigation

Further experiments were performed with live animals (rats). These experiments were performed in a manner that would simulate as close as possible the real situation that is associated with human eyes. In order to do this, fluorescein was finely injected through the back tissues of the rat's eye under the Bruks membrane. The objective was to cause the absorbing material to tightly associate with the relevant tissues under the animal's retina, where the droplets of the AMD pigments would be formed in the case of a human eye. The beam of Ti: Sapphire Ultrafast laser, with an intensity of 40-65 mW, that exited from the slit lamp was then focused under the animal's retina in order to see the bright green spot of fluorescein or A2-E fluorescence.

The goal was, firstly, to see the fluorescent spot from the region under the retina, which is a result of multiphoton excited fluorescence, and secondly, to follow the dynamics of the bleaching of this spot and to see whether it decreases in its intensity as a result of photobleaching. Indeed, in experiments described below, the bright fluorescence spot from the relevant region was seen, with a gradual decrease of the spot intensity.

Figure 14:
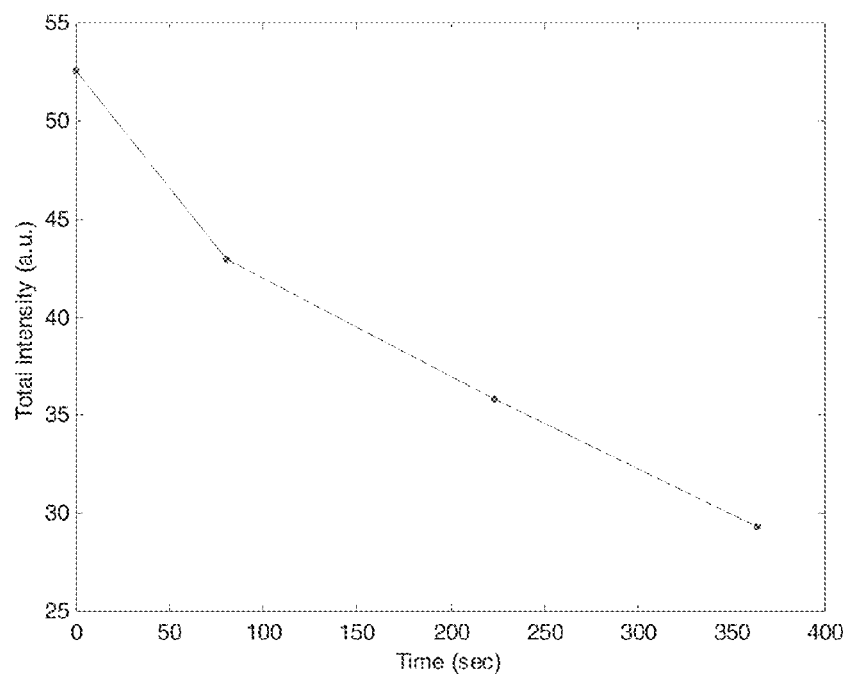
FIG. 14. The relative photobleaching of fluorescein with time for the experiment shown in FIG. 13. From left to right the points represent a different frame in FIG. 13 with the point to the left in this graph corresponding to the top most frame and the point in the extreme right corresponding to the bottom frame in FIG. 13.

In order to check for permanent bleaching, control experiments were performed, where the laser beam was allowed to strike the stained fluorescein tissue for a few seconds, and was allowed to illuminate the spot again after it was blocked for as much as 15-20 min in order to view the effect of dye diffusion in the stained tissue. The fluorescent spot brightness did not change, indicating that there was no fluorescein diffusion to or from the adjacent tissues, and that the only reason that could be responsible for the intensity decrease was photobleaching. The time required for nearly complete photobleaching was on the order of 5-10 min but in seconds the intensity of the fluorescence began to drop as a result of the action of the laser. In the following frames from the simultaneously recorded video, shown in FIG. 13, the typical dynamics of the decrease in the fluorescence intensity is seen (the frames proceed sequentially in time from top, left to bottom right), as photobleaching occurs. The graph shown in FIG. 14 is representative of the typical rate of bleaching for this case. Total intensity is shown at the y-axis, while time is shown in seconds at the x-axis; clearly the intensity of the fluorescence decreased over time due to bleaching. Table 1 shows that the photobleaching rate of A2-E was 100 times faster than that of fluorescein.

Each different type of eye can optionally be monitored with the on-line measurements of physiological viability mentioned above, although it is important to note that these are not the only possible tests for viability. These measurements readily show that there is little or no damage caused to the retina and the adjacent tissues.

A control experiment was also performed, in which the intensity of the Ti:Sapphire laser beam was only increased up to 400 mW, and then focused under the retina as for the experiments described above. Four points under the retina around the central optical nerve were illuminated by the laser beam. The exposure time for each point was 10 min. Also, a larger magnification factor of the slit lamp was used (×25 instead of ×16 used previously) in order to decrease the beam spot size at the retina and to further increase the energy density at these points. Under these conditions, various physiologically relevant tests may optionally be performed for determining the ultra low collateral damage levels that are relevant for disease perturbation (the above exemplary test was performed on these samples; data not shown). The results clearly demonstrated that even for much stronger intensities than in the previous series of experiments, the laser beam intensity caused little or no damage.

In summary, it has been shown that effective photobleaching of dyes including A2-E beneath the retina can be induced, while causing little or no change and/or damage in the retina itself and the surrounding tissue.

REFERENCES

1. G. H. Travis and J. Bennett, Nature Medicine 3, 1196 (1997)

(for numbers shown in parentheses)

[1] Pfeifer, A., and Verma, I. M. (2001). Gene therapy: promises and problems. *Annu Rev Genomics Hum Genet* 2: 177-211.

[2] Aiuti, A., Slavin, S., Aker, M., Ficara, F., Deola, S., Mortellaro, A., Morecki, S., Andolfi, G., Tabucchi, A., Carlucci, F., Marinello, E., Cattaneo, F., Vai, S., Servida, P., Miniero, R., Roncarolo, M. G., and Bordignon, C. (2002). Correction of ADA-SCID by stem cell gene therapy combined with nonmyeloablative conditioning. *Science* 296: 2410-2413.

[3] Hacein-Bey-Abina, S., Le Deist, F., Carlier, F., Bouneaud, C., Hue, C., De Villartay, J. P., Thrasher, A. J., Wulffraat, N., Sorensen, R., Dupuis-Girod, S., Fischer, A., Davies, E. G., Kuis, W., Leiva, L., and Cavazzana-Calvo, M. (2002). Sustained correction of X-linked severe combined immunodeficiency by ex vivo gene therapy. *N Engl J Med* 346: 1185-1193.

[4] Somia, N., and Verma, I. M. (2000). Gene therapy: trials and tribulations. *Nat Rev Genet* 1: 91-99.

[5] Luo, D., and Saltzman, W. M. (2000). Synthetic DNA delivery systems. *Nat Biotechnol* 18: 33-37.

[6] Somiari, S., Glasspool-Malone, J., Drabick, J. J., Gilbert, R. A., Heller, R., Jaroszeski, M. J., and Malone, R. W. (2000). Theory and in vivo application of electroporative gene delivery. *Mol Ther* 2: 178-187.

[7] Taniyama, Y., Tachibana, K., Hiraoka, K., Aoki, M., Yamamoto, S., Matsumoto, K., Nakamura, T., Ogihara, T., Kaneda, Y., and Morishita, R. (2002). Development of safe and efficient novel nonviral gene transfer using ultrasound: enhancement of transfection efficiency of naked plasmid DNA in skeletal muscle. *Gene Ther* 9: 372-380.

[8] Mikszta, J. A., Alarcon, J. B., Brittingham, J. M., Sutter, D. E., Pettis, R. J., and Harvey, N. G. (2002). Improved genetic immunization via micromechanical disruption of skin-barrier function and targeted epidermal delivery. *Nat Med* 8: 415-419.

[9] Opalinska, J. B., and Gewirtz, A. M. (2002). Nucleic-acid therapeutics: basic principles and recent applications. *Nat Rev Drug Discov* 1: 503-514.

[10] Sullenger, B. A., and Gilboa, E. (2002). Emerging clinical applications of RNA. *Nature* 418: 252-258.

[11] Duchler, M., Pengg, M., Schuller, S., Pfneisl, F., Bugingo, C., Brem, G., Wagner, E., Schellander, K., and Muller, M. (2002). Somatic gene transfer into the lactating ovine mammary gland. *J Gene Med* 4: 282-291.

[12] Honigman, A., Zeira, E., Ohana, P., Abramovitz, R., Tavor, E., Bar, I., Zilberman, Y., Rabinovsky, R., Gazit, D., Joseph, A., Panet, A., Shai, E., Palmon, A., Laster, M., and Galun, E. (2001). Imaging transgene expression in live animals. *Mol Ther* 4: 239-249.

[13] Durieux, A. C., Bonnefoy, R., Manissolle, C., and Freyssenet, D. (2002). High-efficiency gene electrotransfer into skeletal muscle: description and physiological applicability of a new pulse generator. *Biochem Biophys Res Commun* 296: 443-450.

[14] Ortiz-Urda, S., Thyagarajan, B., Keene, D. R., Lin, Q., Fang, M., Calos, M. P., and Khavari, P. A. (2002). Stable nonviral genetic correction of inherited human skin disease. *Nat Med* 8: 1166-1170.

[15] Ferber, D. (2001). Gene therapy. Safer and virus-free? *Science* 294: 1638-1642.

[16] Woolf, T. M. (1998). Therapeutic repair of mutated nucleic acid sequences. *Nat Biotechnol* 16: 341-344.

[17] Yant, S. R., Meuse, L., Chiu, W., Ivics, Z., Izsvak, Z., and Kay, M. A. (2000). Somatic integration and long-term transgene expression in normal and haemophilic mice using a DNA transposon system. *Nat Genet* 25: 35-41.

[18] Bartlett, R. J., Stockinger, S., Denis, M. M., Bartlett, W. T., Inverardi, L., Le, T. T., thi Man, N., Morris, G. E., Bogan, D. J., Metcalf-Bogan, J., and Kornegay, J. N. (2000). In vivo targeted repair of a point mutation in the canine dystrophin gene by a chimeric RNA/DNA oligonucleotide. *Nat Biotechnol* 18: 615-622.

[19] Lewin, M., Carlesso, N., Tung, C. H., Tang, X. W., Cory, D., Scadden, D. T., and Weissleder, R. (2000). Tat peptide-derivatized magnetic nanoparticles allow in vivo tracking and recovery of progenitor cells. *Nat Biotechnol* 18: 410-414.

[20] Rebuffat, A., Bernasconi, A., Ceppi, M., Wehrli, H., Verca, S. B., Ibrahim, M., Frey, B. M., Frey, F. J., and Rusconi, S. (2001). Selective enhancement of gene transfer by steroid-mediated gene delivery. *Nat Biotechnol* 19: 1155-1161.

[21] Zhang, G., Budker, V., Williams, P., Subbotin, V., and Wolff, J. A. (2001). Efficient expression of naked dna delivered intraarterially to limb muscles of nonhuman primates. *Hum Gene Ther* 12: 427-438.

[22] Endoh, M., Koibuchi, N., Sato, M., Morishita, R., Kanzaki, T., Murata, Y., and Kaneda, Y. (2002). Fetal gene transfer by intrauterine injection with microbubble-enhanced ultrasound. *Mol Ther* 5: 501-508.

[23] Bettan, M., Emmanuel, F., Darteil, R., Caillaud, J. M., Soubrier, F., Delaere, P., Branelec, D., Mahfoudi, A., Duverger, N., and Scherman, D. (2000). High-level protein secretion into blood circulation after electric pulse-mediated gene transfer into skeletal muscle. *Mol Ther* 2: 204-210.

[24] Lefesvre, P., Attema, J., and Van Bekkum, D. (2002). A comparison of efficacy and toxicity between electroporation and adenoviral gene transfer. *BMC Mol Biol* 3: 12.

[25] Deng, H., Lin, Q., and Khavari, P. A. (1997). Sustainable cutaneous gene delivery. *Nat Biotechnol* 15: 1388-1391.

[26] Babiuk, S., Baca-Estrada, M., Foldvari, M., Storms, M., Rabussay, D., Widera, G., and Babiuk, L. (2002). Electroporation improves the efficacy of DNA vaccines in large animals. *Vaccine* 20: 3399.

[27] Tirlapur, U. K., and Konig, K. (2002). Targeted transfection by femtosecond laser. *Nature* 418: 290-291.

What is claimed is:

1. A method for treating a layer of tissue, comprising:
   selecting a layer of tissue to be targeted, said targeted layer having an overlying layer;
   choosing a laser beam of defined characteristics, wherein said defined characteristics of said laser beam comprise laser pulses within the range of a femtosecond to picoseconds, said laser pulses producing multiphoton laser tissue effects, said laser tissue effects including laser tissue alteration via multiphoton absorption, whereby at every point other than at the targeted layer said laser beam has sufficiently lower fluence than the fluence at the targeted layer; and
   applying said laser beam to the targeted layer, such that the targeted layer is selectively affected by said effects of said laser beam, wherein collateral damage to tissue surrounding the targeted layer is below a preselected threshold.

2. The method of claim 1, wherein said applying comprises porating cells at specific depths in the tissue for inserting genes into said porated cells.

3. The method of claim 1, wherein a biological effect occurring after treatment with said laser beam is monitored for determining at least one in vivo parameter for treating said targeted layer.

4. The method of claim 3, wherein said at least one parameter is determined for treating a specific pathological condition, said specific pathological condition featuring a particular molecular species, according to an effect of said particular molecular species after an injection into a similar live tissue.

5. The method of claim 1, further comprising:
   inserting a gene for expressing a marker.

6. The method of claim 1, further comprising:
   performing a diagnostic assay according to said laser tissue effects.

7. The method of claim 1, wherein said multiphoton laser tissue effects comprise enough energy required to destroy a fungal infection.

8. The method of claim 1, wherein said applying comprises applying enough energy required to treat an infection.

9. The method of claim 1, further comprising:
   introducing a genetic material into said targeted layer.

10. The method of claim 1, further comprising:
    performing laser poration of at least one specific tissue layer with the site specific administration of said laser beam.

11. The method of claim 10, further comprising:
introducing at least one of a macromolecule, a small molecule or a particle into said specific tissue layer.

12. The method of claim 11, wherein said macromolecule comprises at least one of an oligonucleotide, a peptide, a lipid, and a polysaccharide.

13. The method of claim 12, wherein said macromolecule comprises an oligonucleotide, and said oligonucleotide comprises at least one of DNA and RNA.

14. The method of claim 11, wherein said at least one of said macromolecule, said small molecule or said particle further comprises a carrier.

15. The method of claim 14, wherein said at least one of said macromolecule, said small molecule or said particle, and said carrier forms a pharmaceutical composition.

16. The method of claim 15, wherein said pharmaceutical composition comprises at least one material being associated with a specific disease state, for being placed at a specific depth of the tissue to be targeted according to said specific disease state.

17. The method of claim 14, wherein said carrier is formed from at least one macromolecule.

18. The method of claim 14, wherein said carrier encapsulates said macromolecule.

19. The method of claim 14, wherein said carrier and said at least one of said macromolecule, said small molecule or said particle collective form a viral particle or a virus-like particle.

20. The method of claim 1, wherein said multiphoton laser tissue effects are selected to bleach a pigment that is the cause of age related macular degeneration.

21. The method of claim 1, wherein said laser beam is characterized according to a plurality of parameters for permitting the second order term of the expression of a polarizability tensor for describing the interaction of light with matter to be used to perform second harmonic generation, wherein said second harmonic generation arises from the second term of the expansion of the molecular electron polarizability according to the equation $$P = X^{(1)} \cdot E + X^{(2)} \cdot E \cdot E + X^{(3)} \cdot E \cdot E \cdot E + \ldots,$$

wherein P is the polarization, E is the applied electric field, and $X^{(n)}$ are the nth order optical susceptibilities,
whereby collateral damage is below a preselected threshold.

22. The method of claim 21, wherein said laser beam has a wavelength in the range of near infrared to infrared.

23. The method of claim 21, wherein said parameters are at least partially determined according to at least one of a type of tissue to be treated and a type of treatment.

24. The method of claim 21, wherein said laser beam is produced by a tunable laser.

25. The method of claim 1, wherein said laser beam is focused through a lens combination before said applying.

26. A method for monitoring membrane potential with genetically controlled or other markers that allows for membrane potential measurements, comprising targeting a layer of tissue with a laser beam having laser pulses within the range of a femtosecond to picoseconds;
detecting second order effects of an interaction between the targeted layer and said laser, whereby at every point other than at the targeted layer said laser beam has lower fluence than the fluence at the targeted layer; and
monitoring membrane potential in a specific tissue layer by using multiphoton second harmonic generation;
wherein collateral damage to tissue or cellular material not in the monitored membrane being below a preselected threshold.

27. A method according to claim 1, wherein said laser beam has a wavelength in the range of near infrared to infrared.

28. A method according to claim 1, wherein said laser beam has a pulse frequency of 76 mHz.

29. A method according to claim 1, wherein said laser beam has a pulse duration of approximately 200 fsec.

30. A method according to claim 9, wherein said genetic material is introduced into said targeted layer for gene expression.

31. A method according to claim 1, wherein said treating comprises permanently modifying said layer.

32. A method according to claim 1, wherein said collateral damage comprises thermal damage.

33. A method according to claim 1, wherein said laser tissue alteration includes bleaching of pigments.

34. A method according to claim 1, wherein the level of laser power is sufficient for tissue ablation.

35. A method according to claim 1, wherein, after said applying said laser beam to said targeted layer, damage to tissue in said targeted layer is one of transient damage and negligible tissue damage.

36. A method according to claim 1, wherein said laser tissue effects are selected for nonlinear laser tissue interactions in tissues.

37. A method according to claim 1, wherein said targeted layer is several millimeters below a surface layer of the tissue.

38. A method according to claim 1, wherein said targeted layer is located at a depth of one centimeter below the surface of the skin.

39. A method according to claim 25, wherein said lens combination includes a numerical aperture, magnification, and working distance selected such that said lens combination is suitable for the size of the layer of tissue being treated and the depth of the layer.

40. A method according to claim 1, wherein said choosing includes choosing the laser beam according to a plurality of parameters selected from at least one of the current intensity of said laser pulses, the number of said laser pulses, the duration of the laser pulses, the surface laser beam area, and the depth of focus of the laser beam.

41. A method for treating a layer of tissue, comprising:
selecting a layer of tissue to be targeted;
choosing a laser beam of defined characteristics, wherein said defined characteristics of said laser beam comprise laser pulses within the range of a femtosecond to picoseconds, said laser pulses producing multiphoton laser tissue effects, said laser tissue effects including laser tissue alteration via multiphoton absorption, whereby at every point other than at the targeted layer said laser beam has sufficiently lower fluence than the fluence at the targeted layer; and
applying said laser beam to the targeted layer, such that the targeted layer is selectively affected by said effects of said laser beam, wherein collateral damage to tissue surrounding the targeted layer is below a preselected threshold.

* * * * *